US010481467B2

(12) United States Patent
Satoh et al.

(10) Patent No.: US 10,481,467 B2
(45) Date of Patent: Nov. 19, 2019

(54) TERAHERTZ WAVE GENERATION APPARATUS AND INSPECTION APPARATUS

(71) Applicants: Takumi Satoh, Miyagi (JP); Yasuhiro Higashi, Miyagi (JP); Yoshio Wada, Miyagi (JP); Toshiyuki Ikeoh, Miyagi (JP); Yoshiharu Urata, Miyagi (JP)

(72) Inventors: Takumi Satoh, Miyagi (JP); Yasuhiro Higashi, Miyagi (JP); Yoshio Wada, Miyagi (JP); Toshiyuki Ikeoh, Miyagi (JP); Yoshiharu Urata, Miyagi (JP)

(73) Assignees: Ricoh Company, Ltd., Tokyo (JP); PHLUXi, Inc., Miyagi (JP)

( * ) Notice: Subject to any disclaimer, the term of this patent is extended or adjusted under 35 U.S.C. 154(b) by 0 days.

(21) Appl. No.: 15/982,214

(22) Filed: May 17, 2018

(65) Prior Publication Data
US 2018/0335682 A1   Nov. 22, 2018

(30) Foreign Application Priority Data

May 22, 2017   (JP) .................................. 2017-101253

(51) Int. Cl.
*G02F 1/35* (2006.01)
*G01N 21/3586* (2014.01)
*G02F 3/02* (2006.01)

(52) U.S. Cl.
CPC ....... *G02F 1/3534* (2013.01); *G01N 21/3586* (2013.01); *G02F 3/024* (2013.01); *G02F 3/026* (2013.01); *G02F 2203/13* (2013.01)

(58) Field of Classification Search
CPC ..... G02F 1/3534; G02F 3/024; G02F 2203/13
See application file for complete search history.

(56) References Cited

U.S. PATENT DOCUMENTS 6,697,186 B2    2/2004  Kawase et al.
7,054,339 B1 *  5/2006  Hu ........................ G02F 1/3534
                                                                372/12
(Continued)

FOREIGN PATENT DOCUMENTS

CN       205212162 U  *  5/2016  ............. G02F 1/365
JP       2002-072269       3/2002
(Continued)

OTHER PUBLICATIONS

Shikata, et al., "Tunable Terahertz-Wave Parametric Oscillators Using LiNbO3 and MgO: LiNbO3 Crystals", IEEE Transactions on Microwave Theory and Techniques, vol. 48, No. 4, Apr. 2000, pp. 653-661.

*Primary Examiner* — Daniel Petkovsek
(74) *Attorney, Agent, or Firm* — IPUSA, PLLC

(57) ABSTRACT

A terahertz wave generation apparatus includes a plurality of laser light sources configured to generate laser beams respectively having different wavelengths; and a terahertz wave generating element configured to receive the laser beams having different wavelengths and generate a terahertz wave from the laser beams. The plurality of laser light sources include fiber laser light sources respectively including parameters that can be controlled independently, and the terahertz wave generating element includes a nonlinear optical crystal.

10 Claims, 24 Drawing Sheets

(56) References Cited

U.S. PATENT DOCUMENTS

| | | | | |
|---|---|---|---|---|
| 7,551,652 | B1 * | 6/2009 | Jiang | H01S 3/0675 |
| | | | | 372/12 |
| 7,599,409 | B2 * | 10/2009 | Nishizawa | G02F 1/3534 |
| | | | | 372/20 |
| 7,764,422 | B2 | 7/2010 | Ichikawa | |
| 8,476,592 | B2 * | 7/2013 | Jeon | H01S 5/0623 |
| | | | | 250/339.06 |
| 8,497,490 | B2 * | 7/2013 | Ohtake | G02F 1/39 |
| | | | | 250/493.1 |
| 8,584,648 | B2 | 11/2013 | Chiera et al. | |
| 8,610,094 | B2 * | 12/2013 | Kim | G02F 2/002 |
| | | | | 250/493.1 |
| 9,354,484 | B2 * | 5/2016 | Kim | G02F 1/353 |

FOREIGN PATENT DOCUMENTS

| | | |
|---|---|---|
| JP | 6023462 | 9/2012 |
| JP | 2014-215315 | 11/2014 |
| JP | 2016-512914 | 5/2016 |

* cited by examiner

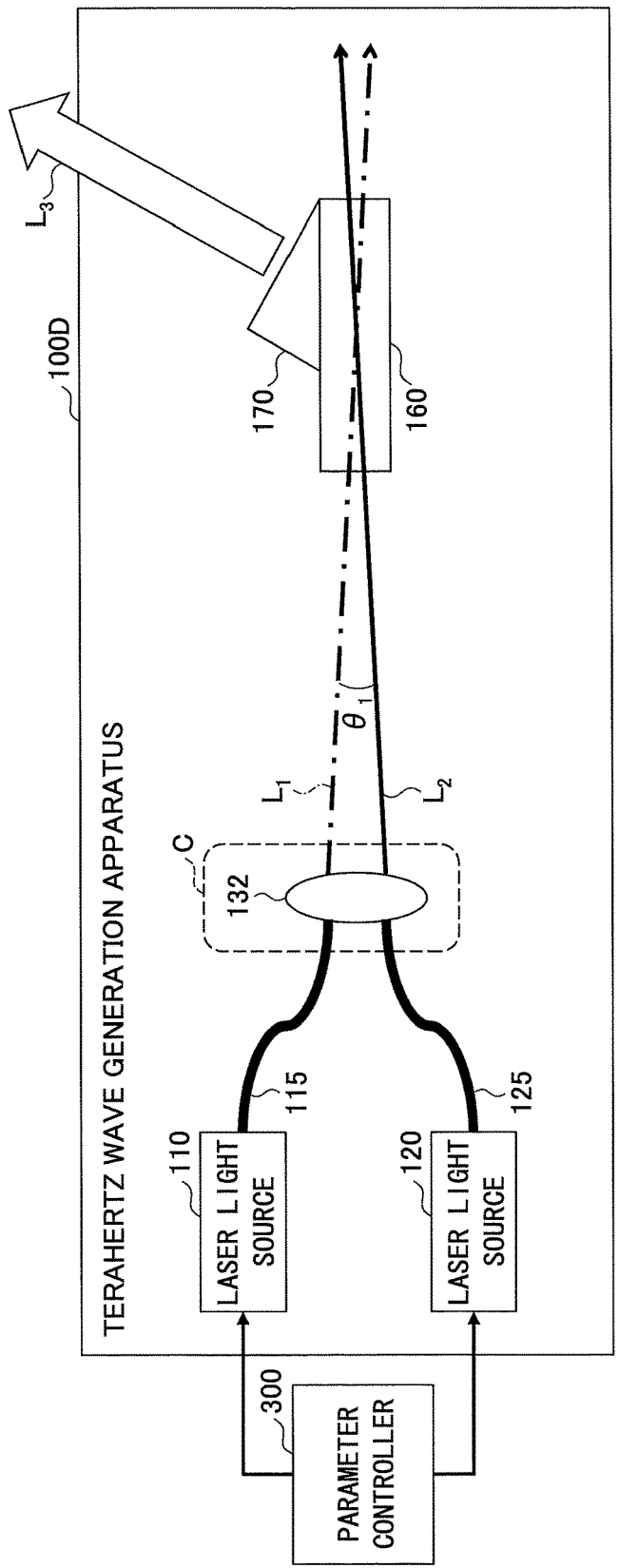

TERAHERTZ WAVE GENERATION APPARATUS AND INSPECTION APPARATUS

CROSS-REFERENCE TO RELATED APPLICATION

The present application claims priority under 35 U.S.C. § 119 to Japanese Patent Application No. 2017-101253, filed on May 22, 2017, the contents of which are incorporated herein by reference in their entirety.

BACKGROUND OF THE INVENTION

1. Field of the Invention

The present invention relates to a terahertz wave generation apparatus and an inspection apparatus.

2. Description of the Related Art

A terahertz wave is an electromagnetic wave having a wavelength of 30 μm to 3000 μm and a frequency of 0.1 THz to 10 THz, and various applications of terahertz waves are expected in the field of basic science, the engineering field, and the medical/biotechnology field, etc.

As a terahertz wave generation apparatus for generating a monochromatic terahertz wave, there are known an apparatus utilizing difference frequency generation by collinear phase matching, an apparatus utilizing parametric generation of non-collinear phase matching, and an apparatus utilizing parametric oscillation of non-collinear phase matching, etc.

As a specific example of the terahertz wave generation apparatus, there is a terahertz wave generation apparatus including first and second cavity dump lasers that respectively output first and second oscillation light pulses from an excitation light pulse output from an excitation light source, and a nonlinear optical crystal that generates a terahertz wave by difference frequency generation of the first and second oscillation light pulses (see, for example, Patent Document 1).

Patent Document 1: Japanese Unexamined Patent Application Publication No. 2014-215315

SUMMARY OF THE INVENTION

An aspect of the present invention provides a terahertz wave generation apparatus and an inspection apparatus, in which one or more of the disadvantages of the related art are reduced.

According to one aspect of the present invention, there is provided a terahertz wave generation apparatus including a plurality of laser light sources configured to generate laser beams respectively having different wavelengths; and a terahertz wave generating element configured to receive the laser beams having different wavelengths and generate a terahertz wave from the laser beams, wherein the plurality of laser light sources include fiber laser light sources respectively including parameters that can be controlled, and the terahertz wave generating element includes a nonlinear optical crystal.

BRIEF DESCRIPTION OF THE DRAWINGS

FIGS. 12A and 12B are diagrams illustrating an example of the configuration of a terahertz wave generation apparatus according to a fifth embodiment of the present invention;

DETAILED DESCRIPTION OF THE PREFERRED EMBODIMENTS

Figure 1:
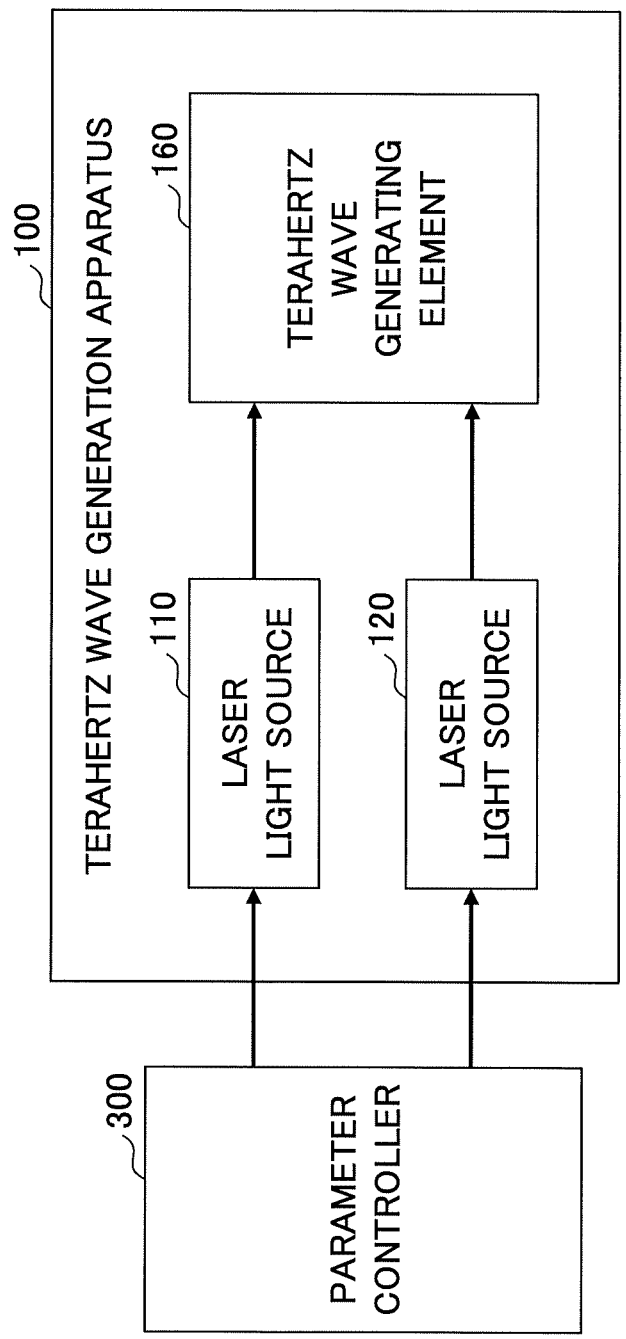
FIG. 1 is a diagram for describing the outline of a terahertz wave generation apparatus according to a first embodiment of the present invention.

The terahertz wave generation apparatus of the related art uses a solid-state laser as a light source, and therefore it has been difficult to control parameters such as the pulse width and the repetition frequency.

A problem to be solved by an embodiment of the present invention is to provide a terahertz wave generation apparatus having excellent parameter controllability.

Embodiments of the present invention will be described by referring to the accompanying drawings. In the specification and drawings of the embodiments, the elements having substantially the same functions are denoted by the same reference numerals, and overlapping descriptions are omitted.

First Embodiment

FIG. 1 is a diagram for describing the outline of a terahertz wave generation apparatus according to a first embodiment. As illustrated in FIG. 1, a terahertz wave generation apparatus 100 includes a laser light source 110, a laser light source 120, and a terahertz wave generating element 160.

The terahertz wave generation apparatus 100 is configured to be connectable to a parameter controller 300, and the laser light sources 110 and 120 are configured to be able to control the parameters independently from the parameter controller 300. The laser light sources 110 and 120 can generate laser beams having different wavelengths (different frequencies) by controlling the parameters independently from the parameter controller 300.

Each of the laser beams emitted from the laser light sources 110 and 120 enters the terahertz wave generating element 160, and the terahertz wave generating element 160 generates a terahertz wave. The frequency of the terahertz wave generated by the terahertz wave generating element 160 is equal to the difference between the frequencies of the respective laser beams emitted from the laser light sources 110 and 120.

Figure 2:
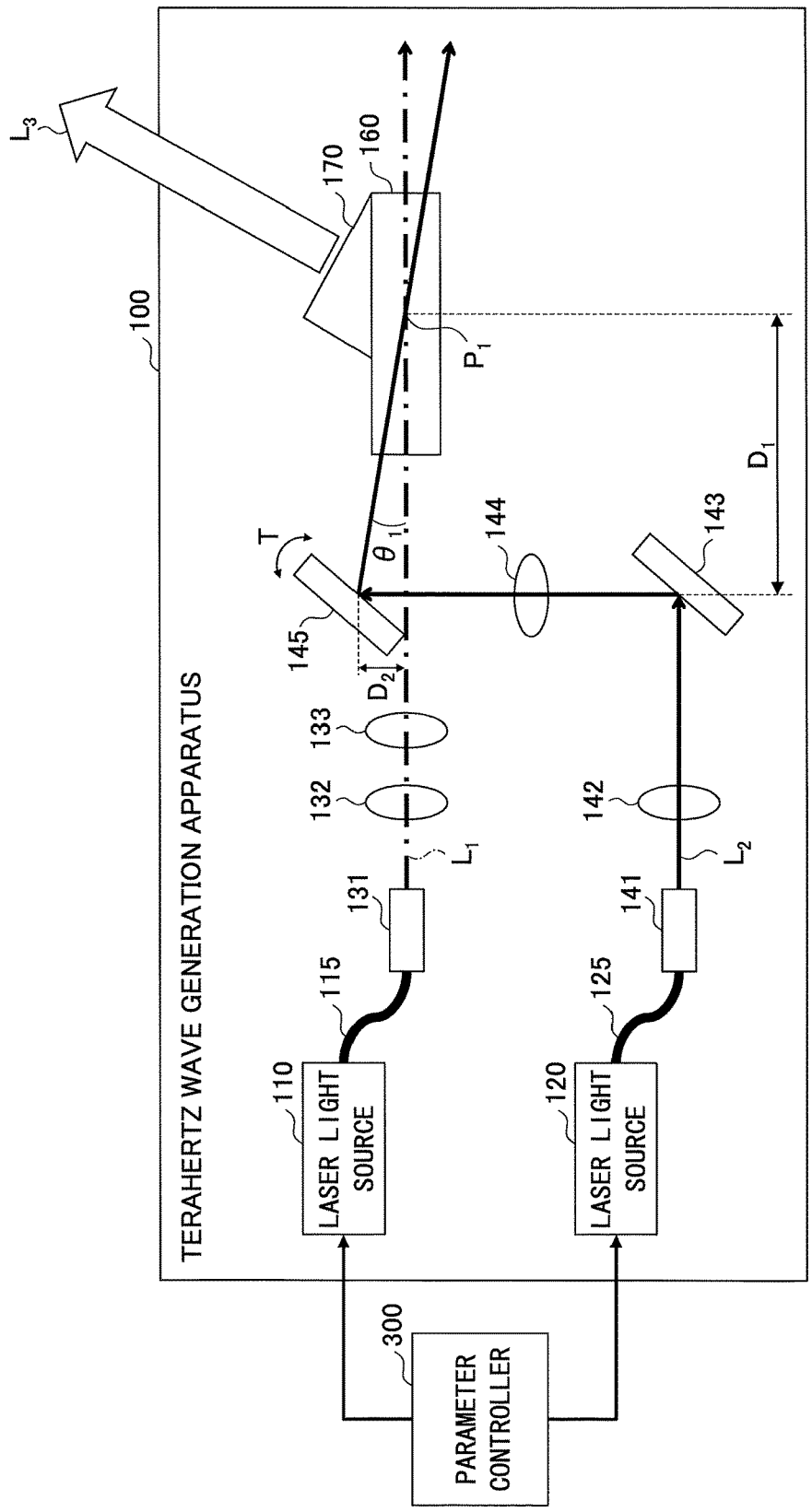
FIG. 2 is a diagram illustrating a configuration of the terahertz wave generation apparatus according to the first embodiment of the present invention.

Hereinafter, a specific configuration of the terahertz wave generation apparatus 100 will be described. FIG. 2 is a diagram illustrating a configuration of the terahertz wave generation apparatus 100 according to the first embodiment. As illustrated in FIG. 2, the terahertz wave generation apparatus 100 includes the laser light sources 110 and 120, isolators 131 and 141, lenses 132 and 133, lenses 142 and 144, mirrors 143 and 145, the terahertz wave generating element 160, and a prism 170.

In the present embodiment, the laser light sources 110 and 120 are fiber laser light sources. The laser light sources 110 and 120 are pulse laser light sources, and are capable of controlling the laser beam generation timing, the wavelength, the pulse width, and the repetition frequency, etc., which are parameters, independently from the parameter controller 300.

As an example, the laser light source 110 has a wavelength regulating range of 1062 nm to 1063.4 nm, a pulse width of 760 ps, an average output of 2.1 W, pulse energy of 10.4 µJ, a peak power of 13.6 kW, and a repetition frequency of 200 kHz.

As an example, the laser light source 120 has a wavelength regulating range of 1064.6 nm to 1066 nm, a pulse width of 760 ps, an average output of 4.2 W, pulse energy of 20.8 µJ, a peak power of 27.4 kW, and a repetition frequency of 200 kHz.

The laser beam $L_1$ (pulse) generated by the laser light source 110 enters the isolator 131 via a delivery fiber 115 (a fiber that emits the laser beam $L_1$). After passing through the isolator 131, the laser beam $L_1$ becomes a vertically polarized light, the laser beam $L_1$ is condensed by the lenses 132 and 133, and the laser beam $L_1$ enters the terahertz wave generating element 160 in parallel with the terahertz wave generating element 160.

The laser beam $L_2$ (pulse) generated by the laser light source 120 enters the isolator 141 via a delivery fiber 125 (a fiber that emits the laser beam $L_2$). After passing through the isolator 141, the laser beam $L_2$ becomes a vertically polarized light, the laser beam $L_2$ is condensed by the lens 142, and the laser beam $L_2$ is incident on the mirror 143. Then, the optical path of the laser beam $L_2$ is changed by the mirror 143, and the laser beam $L_2$ enters the lens 144, the laser beam $L_2$ is condensed by the lens 144, and the laser beam $L_2$ is incident, on the mirror 145. Then, the optical path of the laser beam $L_2$ is further changed by the mirror 145, and the laser beam $L_2$ is obliquely enters the terahertz wave generating element 160.

In the present embodiment, the specifications (focal length, etc.) of the lenses and the arrangements of the optical elements (lenses and mirrors) are set such that when the laser beam $L_1$ and the laser beam $L_2$ enter the terahertz wave generating element 160, the incident angle is $\theta_1$, and the laser beam $L_1$ and the laser beam $L_2$ are condensed at a point $P_1$ inside the terahertz wave generating element 160. The spot size (diameter) of the laser beam $L_1$ at the point $P_1$ is, for example, 0.74 mm, and the spot size (diameter) of the laser beam $L_2$ at the point $P_1$ is, for example, 0.61 mm.

In the present embodiment, as an example, a distance $D_1$ between the position where the laser beam $L_2$ is incident on the mirrors 143 and 145 and the point $P_1$ is 600 mm. Furthermore, a distance $D_2$ between the optical path of the laser beam $L_1$ and the position where the laser beam $L_2$ is incident on the mirror 145 is 10.6 mm.

Furthermore, by adjusting the position and tilting of the mirror 145, it is possible to adjust the incident angle $\theta_1$ and adjust the phase matching angle. For example, by adjusting the wavelength of the laser beam $L_1$ to 1062 nm, the wavelength of the laser beam $L_2$ to 1066 nm, and the incident angle $\theta_1$ to 1.01°, a terahertz wave $L_3$ having a frequency of 1.06 THz can be generated from the terahertz wave generating element 160.

In the present embodiment, as an example, $LiNbO_3$ (lithium niobate: LN), which is a nonlinear optical crystal, is used for the terahertz wave generating element 160. By using the nonlinear optical crystal LN as the terahertz wave generating element 160, it is possible to generate terahertz waves with high efficiency. The terahertz wave $L_3$ generated by the terahertz wave generating element 160 is output to the outside via the prism 170.

Note that as the terahertz wave generating element 160, MgO-doped lithium niobate, which is a nonlinear optical crystal, may be used, or gallium phosphide, which is a nonlinear optical crystal, may be used. When MgO-doped lithium niobate is used for the terahertz wave generating element 160, it is advantageous in terms of resistance to light damage. When gallium phosphide is used for the terahertz wave generating element 160, it is advantageous in that the internal absorption of the terahertz wave is small.

In the terahertz wave generation apparatus 100, the frequency of the terahertz wave $L_3$ can be varied by changing the wavelengths (the wavelengths of the laser beams $L_1$ and $L_2$) of the laser light sources 110 and 120, and by adjusting the incident angle $\theta_1$ to an appropriate value.

In order to adjust the incident angle $\theta_1$, an incident angle changing means is to be provided. For example, the incident angle changing means translates the mirror 145 in a direction perpendicular to the optical axis of the laser beam $L_1$ to change the distance $D_2$. Then, the mirror 145 is rotated in the direction of the arrow T so as to converge the laser beam $L_2$ to the point $P_1$ in order to correct the shift of the converging position of the laser beam $L_2$ in the terahertz wave generating element 160.

The translational movement of the mirror 145 can be implemented by, for example, a direct-acting stage to which a motor is attached, a piezo, or a voice coil motor, etc. The rotation (circular movement) of the mirror 145 can be implemented by, for example, a gonio stage or a rotation stage, etc. The automatic position adjustment by a stepping motor, etc., may also be performed.

The wavelengths of the laser light sources 110 and 120 are changed by changing the temperature of the laser light sources 110 and 120. A description is given of an example in which the laser light sources 110 and 120 are a Master Oscillator Power Amplifier (MOPA) type fiber laser light source that directly modulates a semiconductor laser of a Distributed Feedback (DFB) type that is a seed laser.

Figure 3A:
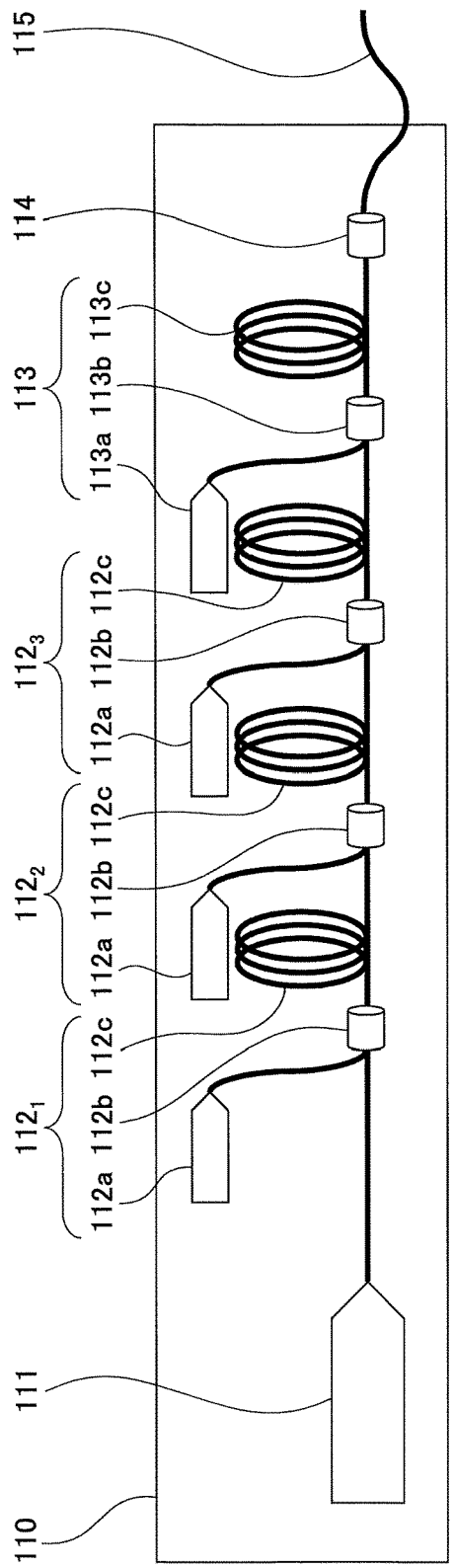
FIGS. 3A and 3B are diagrams illustrating examples of specific configurations of laser light sources used in the terahertz wave generation apparatus according to the first embodiment of the present invention.
Figure 3B:
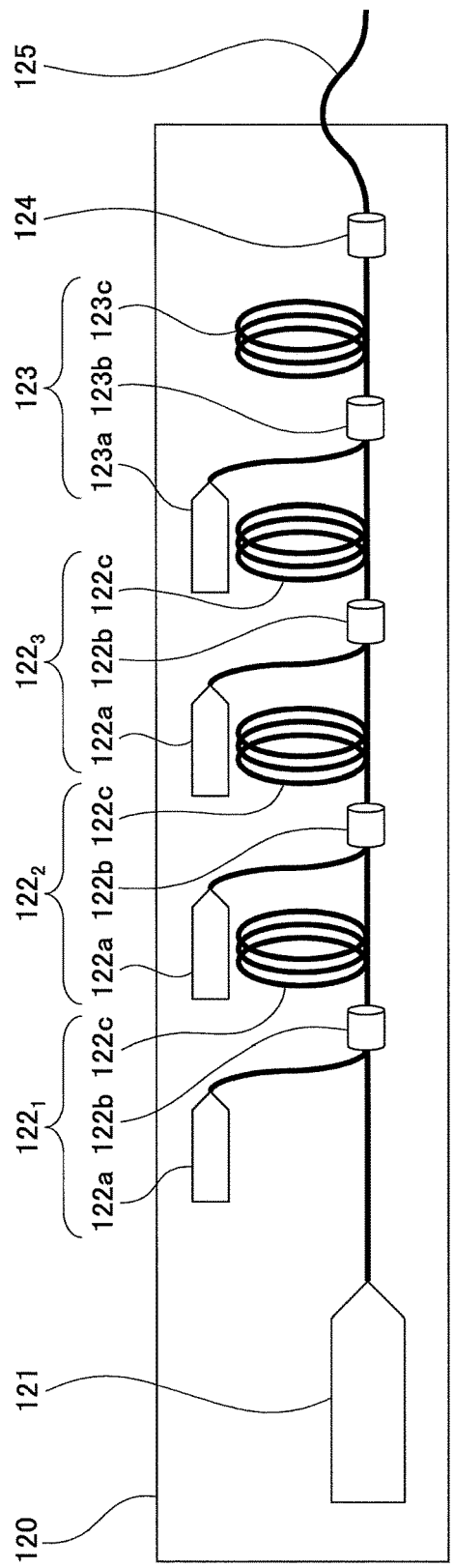

FIGS. 3A and 3B are diagrams illustrating examples of specific configurations of laser light sources used in the terahertz wave generation apparatus according to the first embodiment. The laser light source 110 illustrated in FIG. 3A pulse-oscillates a seed laser light source 111 to generate a seed light, amplifies the seed light in multiple stages with a fiber amplifier including preamplifiers $112_1$, $112_2$, and $112_3$ and a main amplifier 113 connected in series, and outputs the seed light via the a coupler 114 and the delivery fiber 115.

Each of the preamplifiers $112_1$, $112_2$, and $112_3$ includes an excitation laser light source 112a, a coupler 112b, and an optical fiber 112c, and the main amplifier 113 includes an excitation laser light source 113a, a coupler 113b, and an optical fiber 113c.

Similarly, the laser light source 120 illustrated in FIG. 3B pulse-oscillates a seed laser light source 121 to generate a seed light, amplifies the seed light in multiple stages with a fiber amplifier including preamplifiers $122_1$, $122_2$, and $122_3$ and a main amplifier 123 connected in series, and outputs the seed light via the a coupler 124 and a delivery fiber 125.

Each of the preamplifiers $122_1$, $122_2$, and $122_3$ includes an excitation laser light source 122a, a coupler 122b, and an optical fiber 122c, and the main amplifier 123 includes an excitation laser light source 123a, a coupler 123b, and an optical fiber 123c.

As the excitation laser light sources 112a, 113a, 122a, and 123a, for example, a DFB type semiconductor laser may be used. As the optical fibers 112c, 113c, 122c, and 123c, for example, a fiber in which ytterbium (Yb) is doped, may be used. Note that the number of stages of the preamplifier is not limited to three stages, and may be any number of stages.

Figure 4:
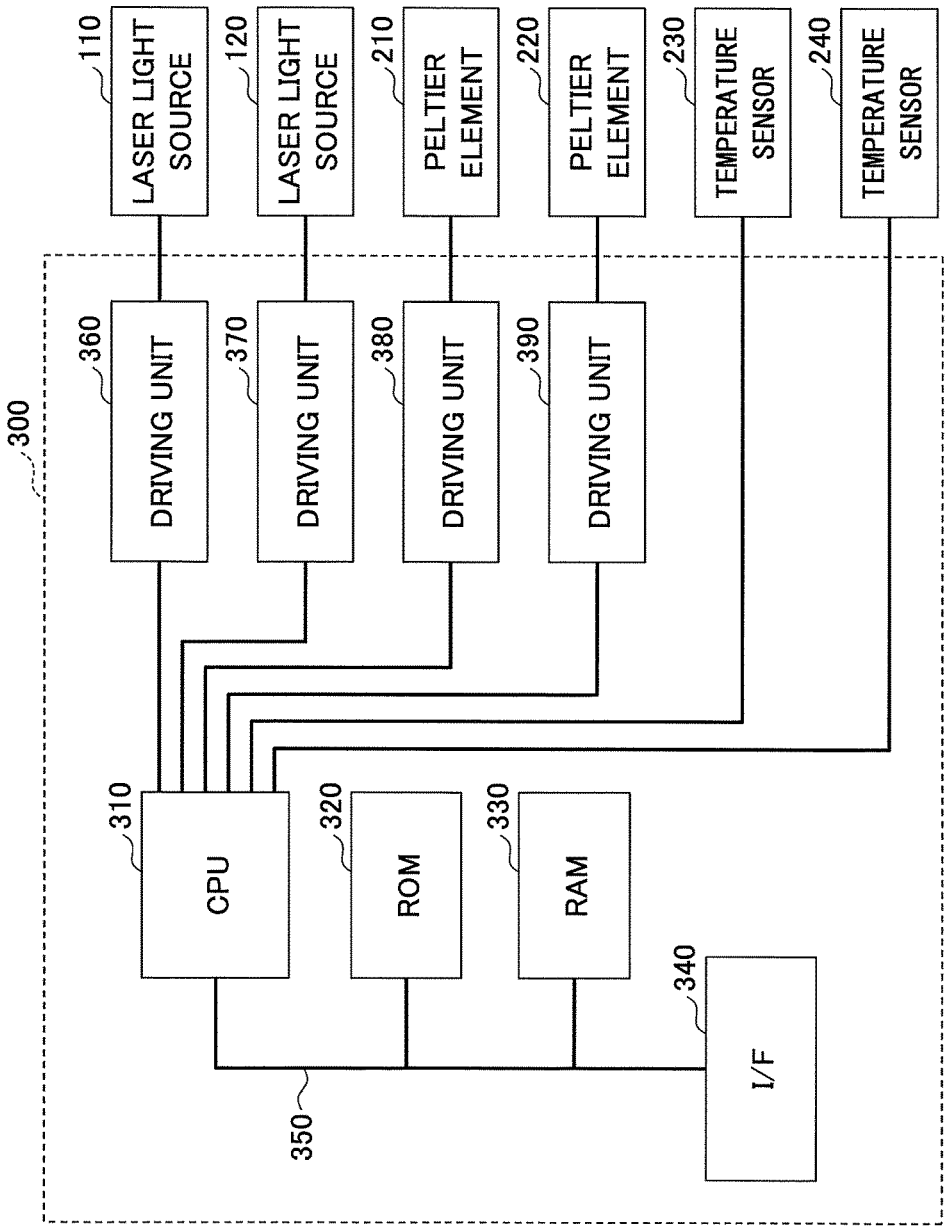
FIG. 4 is an example of a hardware block diagram of a parameter controller according to the first embodiment of the present invention.

FIG. 4 is an example of a hardware block diagram of the parameter controller. As illustrated in FIG. 4, the parameter controller 300 includes, for example, a central processing unit (CPU) 310, a read-only memory (ROM) 320, a random access memory (RAM) 330, an interface (I/F) 340, a bus line 350, and driving units 360 to 390. The CPU 310, the ROM 320, the RAM 330, and the I/F 340 are mutually connected via the bus line 350.

The CPU 310 controls each function of the parameter controller 300. The ROM 320 that is a storage means stores programs executed by the CPU 310 to control the respective functions of the parameter controller 300, and various kinds of information. The RAM 330 that is a storage means is used as a work area, etc., of the CPU 310.

Furthermore, the RAM 330 can temporarily store predetermined information. The I/F 340 is an interface for connecting the parameter controller 300 to another device, etc. The parameter controller 300 may be connected to an external network, etc., via the I/F 340.

Figure 5:
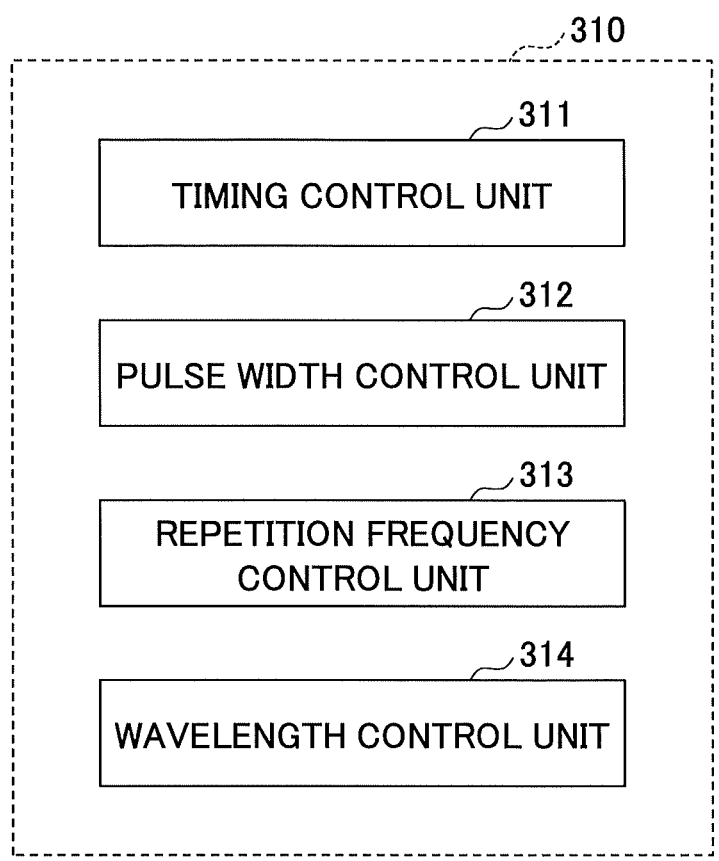
FIG. 5 is an example of a functional block diagram of a CPU of the parameter controller according to the first embodiment of the present invention.

FIG. 5 is an example of a functional block diagram of the CPU of the parameter controller 300. As illustrated in FIG. 5, the CPU 310 includes a timing control unit 311, a pulse width control unit 312, a repetition frequency control unit 313, and a wavelength control unit 314, as functional blocks. The CPU 310 may include other functional blocks as appropriate.

The timing control unit 311 sends a trigger signal to the driving units 360 and 370 to generate the laser beam $L_1$ from the laser light source 110 and generate the laser beam $L_2$ from the laser light source 120. By sending a trigger signal to the driving units 360 and 370, the timing control unit 311 can voluntarily control the ON/OFF of the terahertz wave generated in the terahertz wave generating element 160.

The timing at which the timing control unit 311 sends a trigger signal to the driving unit 360 and the timing control unit 311 sends a trigger signal to the driving unit 370 can be set to be any timing; however, the timings of sending trigger signals to the driving units 360 and 370 are adjusted such that at the point $P_1$, which is the light condensing position inside the terahertz wave generating element 160, the mutual pulses (the laser beams $L_1$ and $L_2$) overlap with each other.

The pulse width control unit 312 can instruct the driving units 360 and 370 to vary the time width of one pulse of the driving signals (pulse train) supplied from the driving units 360 and 370 to the laser light sources 110 and 120, and control the pulse width of the laser beam $L_1$ emitted from the laser light source 110 and the pulse width of the laser beam $L_2$ emitted from the laser light source 120.

The repetition frequency control unit 313 can instruct the driving units 360 and 370 to vary the number of pulses per second of the driving signals (pulse train) supplied from the driving units 360 and 37Q to the laser light sources 110 and 120, and control the repetition frequency of the laser beam $L_1$ emitted from the laser light source 110 and the repetition frequency of the laser beam $L_2$ emitted from the laser light source 120.

The wavelength control unit 314 can instruct the driving unit 380 to supply a driving signal from the driving unit 380 to a Peltier element 210 so as to control the wavelength of the laser beam $L_1$ emitted from the laser light source 110. Specifically, the Peltier element 210 is driven based on the temperature detected by a temperature sensor 230 to control the laser light source 110 to have a predetermined temperature.

Similarly, the wavelength control unit 314 can instruct the driving unit 390 to supply a driving signal from the driving unit 390 to the Peltier element 220, and control the wavelength of the laser beam $L_2$ emitted from the laser light source 120. Specifically, the Peltier element 220 is driven based on the temperature detected by a temperature sensor 240 to control the laser light source 120 to have a predetermined temperature.

Note that the pulse width, the repetition frequency, and the wavelength of the laser beams $L_1$ and $L_2$ are determined by the pulse width, the repetition frequency, and the wavelength of the seed laser light sources 111 and 121. The wavelengths of the seed laser light sources 111 and 121 can be varied by changing the controlled temperature of the seed laser light sources 111 and 121.

Therefore, it is preferable to dispose the Peltier element 210 and the temperature sensor 230 near the seed laser light source 111 of the laser light source 110, and dispose the Peltier element 220 and the temperature sensor 240 near the seed laser light source 121 of the laser light source 120. However, when the wavelengths of the laser light sources 110 and 120 are not controlled, the Peltier elements 210 and 220 and the temperature sensors 230 and 240 do not have to be provided.

Figure 6:
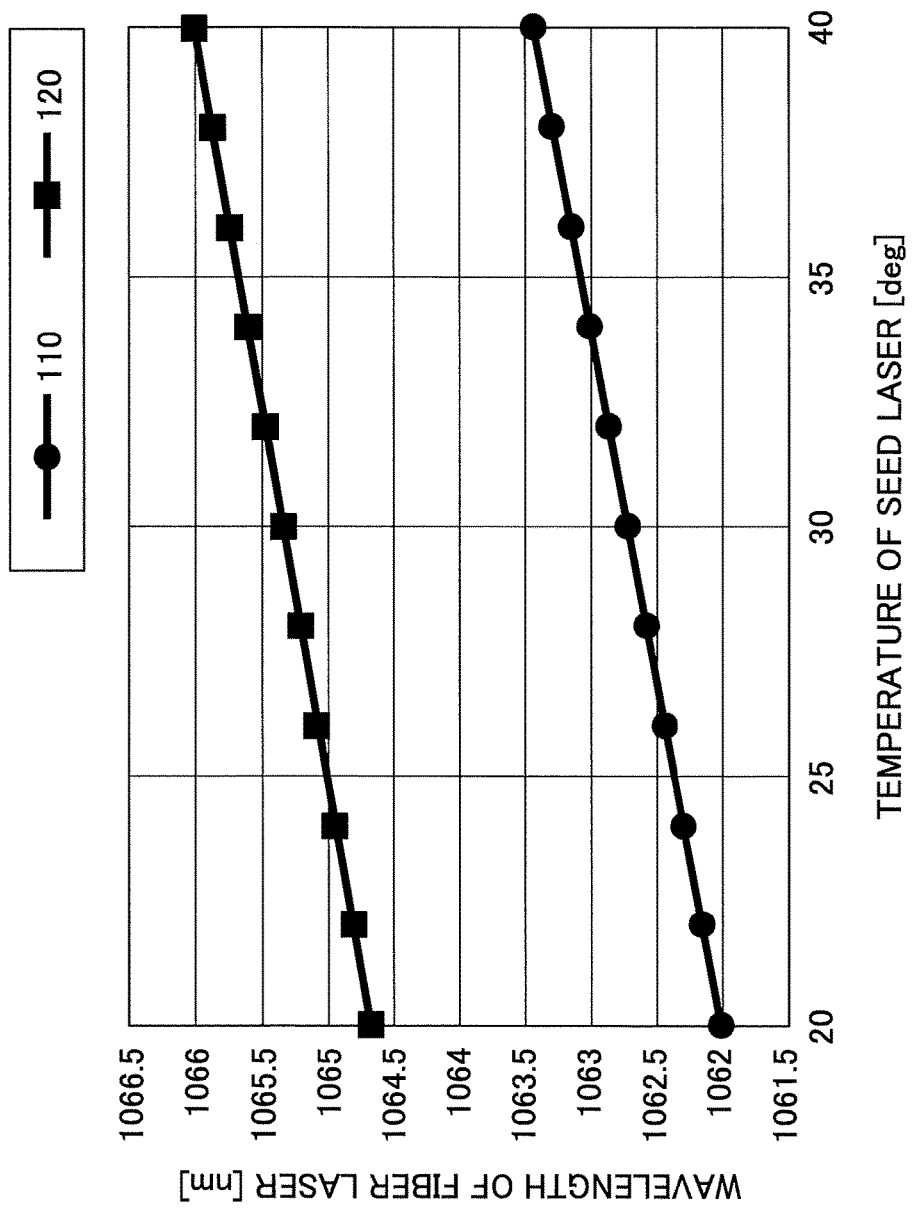
FIG. 6 is a diagram illustrating an example of the relationship between the wavelength of a fiber laser and the temperature of a seed laser according to the first embodiment of the present invention.

FIG. 6 is a diagram illustrating an example of the relationship between the wavelength of the fiber laser and the temperature of the seed laser. In FIG. 6, a circle represents the relationship between the wavelength of the laser light source 110 (fiber laser) and the temperature of the seed laser light source 111, and a square represents the relationship between the wavelength of the laser light source 120 (fiber laser) and the temperature of the seed laser light source 121.

As illustrated in FIG. 6, the laser light source 110 oscillates at a wavelength of around 1062 nm, and the laser light source 120 oscillates at a wavelength of around 1066 nm. The oscillation wavelength of the laser light source 110 can be changed according to the temperature of the seed laser light source 111, the oscillation wavelength of the laser light source 120 can be changed according to the temperature of the seed laser light source 121, and the inclination of each of these oscillation wavelengths is approximately 0.07 nm/° C.

For example, when the controlled temperature of the seed laser light source 111 is set to 20° C., the oscillation wavelength of the laser light source 110 is 1062.01 nm. Furthermore, when the controlled temperature of the seed laser light source 121 is set to 40° C., the oscillation wavelength of the laser light source 120 is 1065.992 nm. At this time, the oscillation frequency of the terahertz wave $L_3$ generated from the terahertz wave generating element 160, is determined by the difference frequency between the oscillation frequencies of the laser light source 110 and the laser light source 120, and the oscillation frequency of the terahertz wave $L_3$ is calculated to be 1.054 THz.

Figure 7:
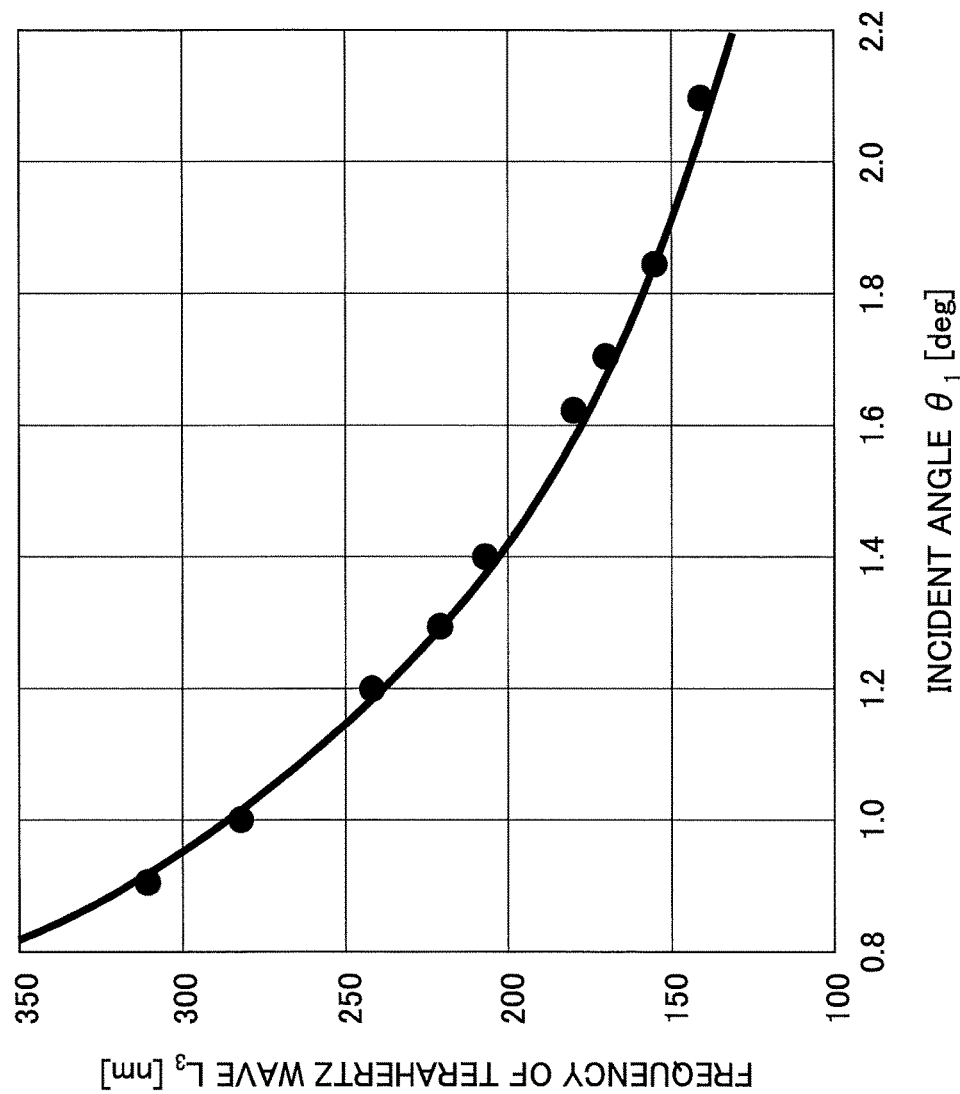
FIG. 7 is a diagram illustrating an example of the relationship between an incident angle and the wavelength of a terahertz wave according to the first embodiment of the present invention.

FIG. 7 is a diagram illustrating an example of the relationship between the incident angle $\theta_1$ and the wavelength of the terahertz wave $L_3$, and illustrates a case where LN is used as the nonlinear crystal forming the terahertz wave generating element. Note that FIG. 7 is excerpted from Shikata, et al., *IEEE Transactions on Microwave Theory and Techniques*, volume. 48, no. 4, April 2000, pp. 653-661. As indicated in FIG. 7, when LN is used as the nonlinear crystal forming the terahertz wave generating element, the incident angle $\theta_1$ for generating a terahertz wave of 1.054 THz (wavelength 284.3 μm) is approximately 1.01°.

The controlled temperature of the seed laser light sources 111 and 121 can be changed between 20° C. to 40° C. However, by setting the controlled temperature of the seed laser light source 111 to 40° C., and setting the controlled temperature of the seed laser light source 121 to 20° C., it is possible to generate the terahertz wave $L_3$ of 0.324 THz. That is, in the terahertz wave generation apparatus 100, it is possible to generate the terahertz wave $L_3$ of any size from 0.324 THz to 1.054 THz, by changing the controlled temperature of the seed laser light sources 111 and 121.

Note that when Yb is doped in the optical fibers 112c, 113c, 122c, and 123c forming the fiber amplifier, the laser beams $L_1$ and $L_2$ have wavelengths in the vicinity of 1000 nm to 1200 nm; however, Er (erbium) may be doped, instead of Yb, in each of the optical fibers forming the fiber amplifier, such that the laser beams $L_1$ and $L_2$ have a wavelength in the vicinity of 1500 nm to 1650 nm. Alternatively, Tm (thulium) may be doped, instead of Yb, in each of the optical fibers forming the fiber amplifier, such that the laser beams $L_1$ and $L_2$ have a wavelength in the vicinity 1800 nm to 2000 nm.

As described above, in the terahertz wave generation apparatus 100, a fiber laser light source that can independently control the parameters is adopted as the laser light sources 110 and 120. This makes it possible to improve the controllability of the parameters such as the wavelength (frequency) and the incident timing of the laser beam incident on the terahertz wave generating element 160, and by adjusting the phase matching angle, it is possible to efficiently generate a terahertz wave of any size.

Furthermore, by using a pulse laser light source as the laser light sources 110 and 120, a terahertz wave having high peak power can be generated.

Furthermore, by using a Master Oscillator Power Amplifier (MOPA) type fiber laser light source as the laser light sources 110 and 120, it is possible to easily control the wavelength by controlling the temperature of the seed laser light source, and furthermore, it is possible to easily control the drive current.

Furthermore, in the example described above, the laser light sources 110 and 120 have a pulse width of 760 ps and a repetition frequency of 200 kHz; however, the present invention is not limited as such. The pulse width and the repetition frequency can be changed by electrically controlling the oscillation of the seed laser light sources 111 and 121 by the parameter controller 300 provided outside the terahertz wave generation apparatus 100, and a pulse width of approximately 10 ps to 10 ns and a repetition frequency of approximately 100 KHz to 100 MHz can be realized.

By using a pulse laser light source whose pulse width can be varied, the efficiency of the terahertz wave to be generated can be controlled. Furthermore, by using a pulse laser light source whose repetition frequency can be varied, it is possible to control the pulse energy of the terahertz wave to be generated. Furthermore, by varying the parameters by implementing electrical control, the parameters can be easily controlled with high accuracy in a wide range.

Second Embodiment

In a second embodiment, a description is given of an example in which the terahertz wave generation apparatus is reduced in size and a wider range of terahertz waves are generated. Note that in the second embodiment, descriptions of the same elements as those in the embodiment described above, may be omitted.

Figure 8:
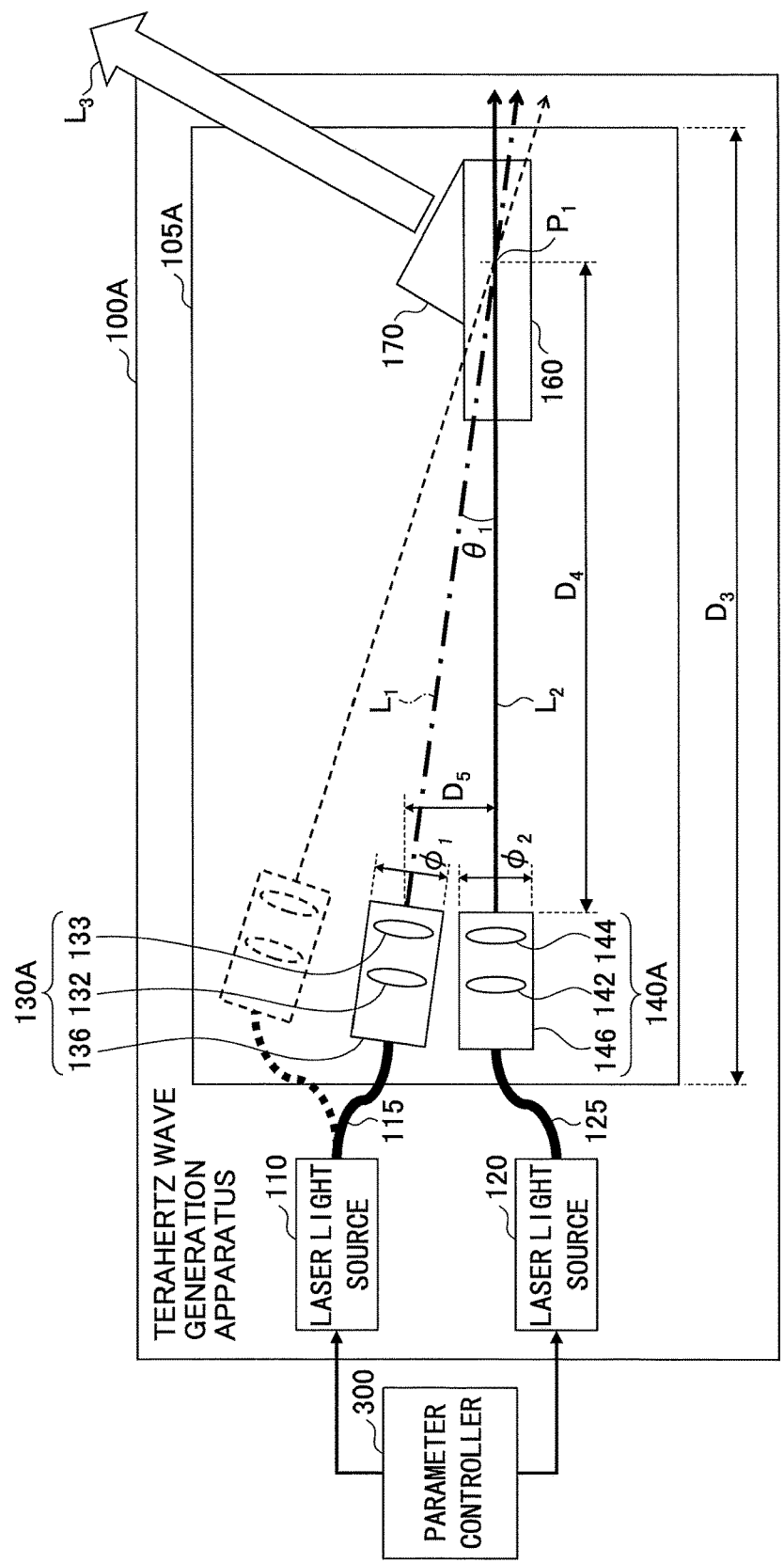
FIG. 8 is a diagram illustrating an example of a configuration of a terahertz wave generation apparatus according to a second embodiment of the present invention.

FIG. 8 is a diagram illustrating an example of a configuration of a terahertz wave generation apparatus according to the second embodiment. As illustrated in FIG. 8, a terahertz wave generation apparatus 100A includes the laser light sources 110 and 120, optical elements 130A and 140A, the terahertz wave generating element 160, and a prism 170. The optical elements 130A and 140A and the terahertz wave generating element 160 are accommodated in a casing 105A having a length $D_3$ of 300 mm in the optical axis direction of the laser beam $L_2$, for example.

The minute optical element 130A is disposed at the output end portion of the delivery fiber 115 and the minute optical element 140A is disposed at the output end portion of the delivery fiber 125. For example, the optical element 130A has a structure in which a lens array including the lenses 132 and 133 is disposed in a holder 136, and the output end portion of the holder 136 has a circular shape having a diameter of $\varphi_1=3$ mm. Similarly, for example, the optical element 140A has a structure in which a lens array including the lenses 142 and 144 is disposed in a holder 146, and the output end portion of the holder 146 has a circular shape having a diameter of $\varphi_2=3$ mm.

In this case, for example, the point $P_1$, which is the light condensing position inside the terahertz wave generating element 160, is located at a position of $D_4=200$ mm from the output end portion (laser output end portion) of the holders 136 and 146. The oscillation wavelength of the terahertz wave $L_3$ to be generated is determined depending on the oscillation wavelength of the seed laser light source and the incident angle $\theta_1$ to the terahertz wave generating element 160. In a case where the output end portions $\varphi_1$ and $\varphi_2$ of the holders 136 and 146 have a diameter of 3 mm, an interval $D_5$ between the optical axes of the holders 136 and 146 cannot be brought 3 mm or less, and therefore the incident angle $\theta_1$ is approximately 0.86° at minimum.

Similar to the first embodiment, it is possible to change the frequency of the terahertz wave $L_3$ to be generated, by changing the temperature of the seed laser light sources 111 and 121 and changing the incident angle $\theta_1$ so as to satisfy the phase matching condition. In the present embodiment, the changing of the incident angle $\theta_1$ is performed by rotating the optical element 130A along a circular arc having a radius of 200 mm around the point $P_1$, which is the focal point of the laser beam $L_1$ and the laser beam $L_2$.

For example, when the frequency of the terahertz wave $L_3$ is 3 THz, the wavelength of the laser light source 110 may be set to 1061.6 nm, the wavelength of the laser light source 120 may be set to 1072.0 nm, and the incident angle $\theta_1$ may be set to 2.9°.

The incident angle changing means for adjusting the incident angle $\theta_1$ is not particularly limited as long as the incident angle changing means is a mechanical mechanism for circularly moving the optical element 130A, and for example, a gonio stage and a rotating stage, etc., may be used. Furthermore, automatic position adjustment by a stepping motor, etc., may also be performed.

As described above, by incorporating the minute optical elements 130A and 140A at the output end portions of the delivery fibers 115 and 125, the laser light sources 110 and 120 can be disposed close to each other. Accordingly, it is possible to simplify the optical system and to reduce the size of the terahertz wave generation apparatus 100A.

Figure 9A:
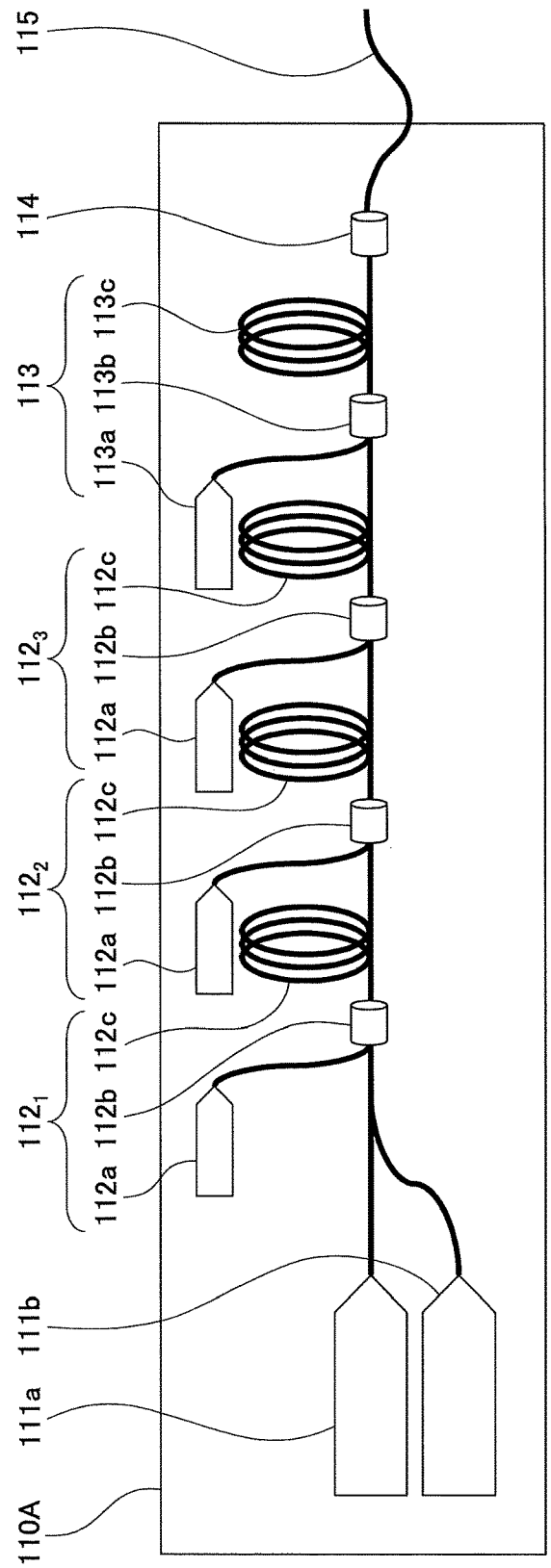
FIGS. 9A and 9B are diagrams illustrating examples of specific configurations of the laser light sources used in the terahertz wave generation apparatus according to the second embodiment of the present invention.
Figure 9B:
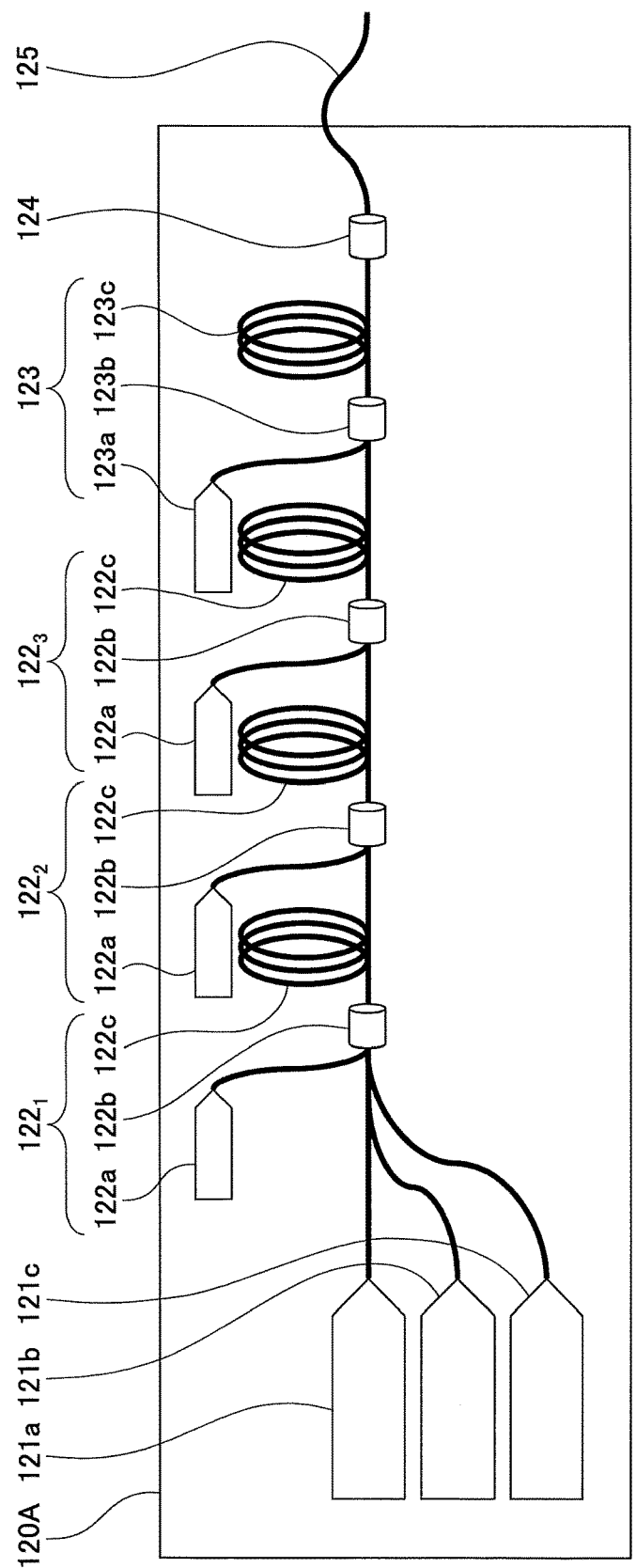

Furthermore, by using laser light sources 110A and 120A illustrated in FIGS. 9A and 9B instead of the laser light sources 110 and 120, it is possible to generate the terahertz wave $L_3$ having a wider range. FIGS. 9A and 9B are diagrams illustrating examples of specific configurations of the laser light sources 110A and 120A, respectively. Similar to the laser light sources 110 and 120, the laser light sources 110A and 120A illustrated in FIGS. 9A and 9B are MOPA type fiber lasers.

The laser light source 110A differs from the laser light source 110 (see FIG. 3) in that the laser light source 110A includes two seed laser light sources 111a and 111b, and is otherwise the same as the laser light source 110. Furthermore, the laser light source 120A differs from the laser light source 120 (see FIG. 3) in that the laser light source 120A includes three seed laser light sources 121a, 121b, and 121c, and is otherwise the same as the laser light source 120.

The seed laser light sources 111a and 111b and the seed laser light sources 121a, 121b, and 121c are respectively connected to the parameter controller 300, and can perform parameter control independently of the parameter controller 300. Here, as an example, it is assumed that the controlled temperatures of the seed laser light sources 111a and 111b and the seed laser light sources 121a, 121b, and 121c can be changed between 20° C. to 40° C.

In the present embodiment, as an example, the center wavelength of the seed laser light source 111a is 1062 nm, and the center wavelength of the seed laser light source 111b is 1064 nm. Furthermore, the center wavelength of the seed laser light source 121a is 1064 nm, the center wavelength of the seed laser light source 121b is 1068 nm, and the center wavelength of the seed laser light source 121c is 1072 nm. Note that the center wavelength is the wavelength of each laser when the controlled temperature is set to 30° C.

TABLE 1

| SEED LASER COMBINATION | SEED LASER | SEED LASER WAVELENGTH (nm) | | | TERAHERTZ WAVE $L_3$ FREQUENCY (THz) | |
| --- | --- | --- | --- | --- | --- | --- |
| | | CENTRAL TEMPERATURE (30° C.) | MINIMUM TEMPERATURE (20° C.) | MAXIMUM TEMPERATURE (40° C.) | MINIMUM | MAXIMUM |
| 1 | 111a | 1062 | 1061.3 | 1062.7 | 0.159 | 0.902 |
| | 121a | 1064 | 1063.3 | 1064.7 | | |
| 2 | 111b | 1064 | 1063.3 | 1064.7 | 0.686 | 1.425 |
| | 121b | 1068 | 1067.3 | 1068.7 | | |
| 3 | 111a | 1062 | 1061.3 | 1062.7 | 1.216 | 1.956 |
| | 121b | 1068 | 1067.3 | 1068.7 | | |
| 4 | 111b | 1064 | 1063.3 | 1064.7 | 1.735 | 2.471 |
| | 121c | 1072 | 1071.3 | 1072.7 | | |
| 5 | 111a | 1062 | 1061.3 | 1062.7 | 2.265 | 3.002 |
| | 121c | 1072 | 1071.3 | 1072.7 | | |

In this case, as indicated in Table 1, the frequency of the terahertz wave $L_3$, which can be generated by the combination of the seed laser light source 111a and the seed laser light source 121a, is in a range of 0.159 THz to 0.902 THz. Similarly, the frequency of the terahertz wave $L_3$, which can be generated by the combination of the seed laser light source 111b and the seed laser light source 121b, is in a range of 0.686 THz to 1.425 THz.

Similarly, the frequency of the terahertz wave $L_3$, which can be generated by the combination of the seed laser light source 111a and the seed laser light source 121b, is in a range of 1.216 THz to 1.956 THz. Similarly, the frequency of the terahertz wave $L_3$, which can be generated by the combination of the seed laser light source 111b and the seed laser light source 121c, is in a range of 1.735 THz to 2.471 THz.

Similarly, the frequency of the terahertz wave $L_3$, which can be generated by the combination of the seed laser light source 111a and the seed laser light source 121c, is in a range of 2.265 THz to 3.002 THz.

As described above, it is possible to generate the terahertz wave $L_3$ having a wider range, by having the laser light sources 110A and 120A each including a plurality of seed laser light sources, and setting optimum conditions in accordance with the oscillation wavelength of the terahertz wave $L_3$ to be generated.

Furthermore, by electrically switching on/off of a plurality of seed laser light sources of the laser light sources 110A and 120A at high speed, it is possible to implement high-speed switching of the terahertz wave $L_3$ in a stepwise manner, which cannot be achieved by wavelength selection by temperature control.

Note that the number of seed laser light sources included in the laser light sources 110A and 120A is not limited to the above example, and can be determined to be any number.

Third Embodiment

In the third embodiment, an example of further reducing the size of the terahertz wave generation apparatus will be described. Note that in the third embodiment, descriptions of the same elements as those in the embodiments described above, may be omitted.

Figure 10A:
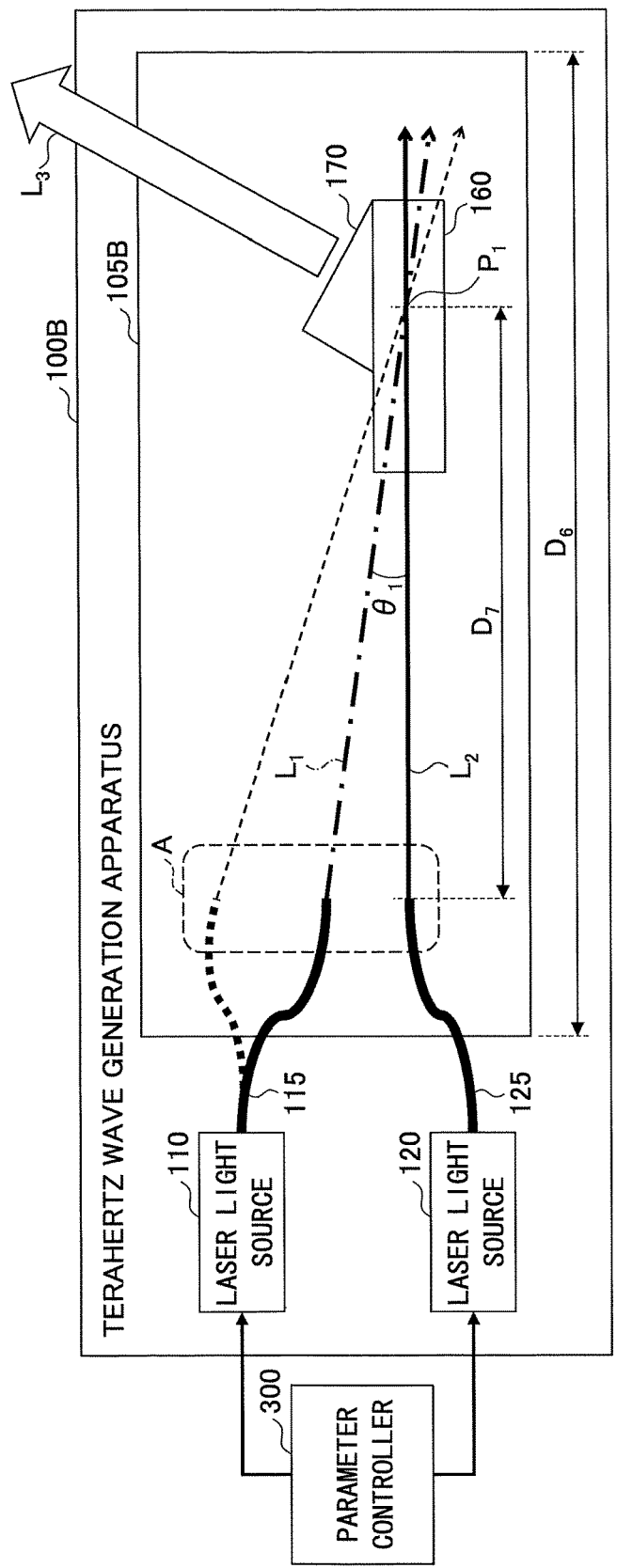
FIGS. 10A and 10B are diagrams illustrating an example of a configuration of a terahertz wave generation apparatus according to a third embodiment of the present invention.
Figure 10B:
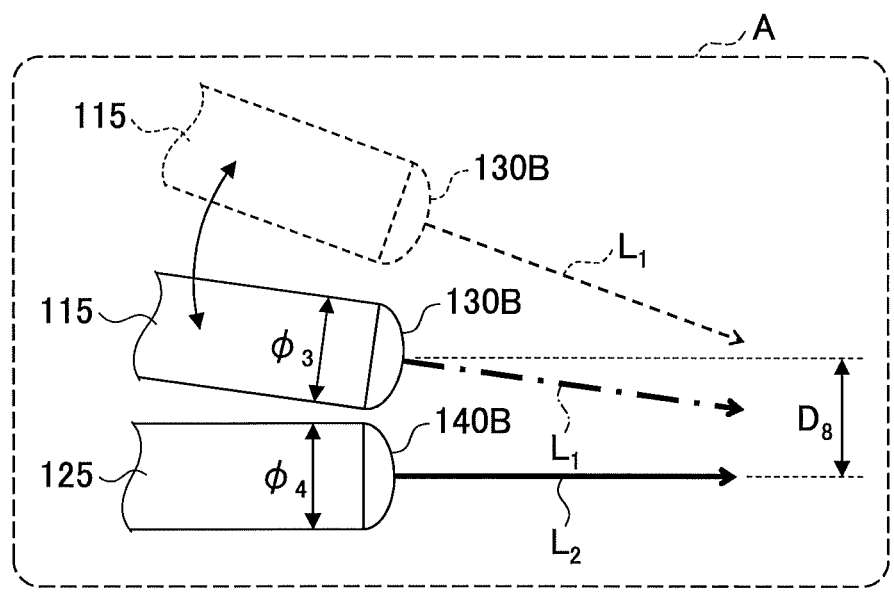

FIGS. 10A and 10B are diagrams illustrating an example of a configuration of a terahertz wave generation apparatus according to a third embodiment, wherein FIG. 10A is an overall view and FIG. 10B is an enlarged view of a portion A in FIG. 10A.

As illustrated in FIG. 10A, a terahertz wave generation apparatus 100B includes the laser light sources 110 and 120, lenses 130B and 140B, the terahertz wave generating element 160, and the prism 170. The lenses 130B and 140B and the terahertz wave generating element 160 are accommodated in a casing 105B having a length $D_6$ of 100 mm in the optical axis direction of the laser beam $L_2$, for example.

At the output end portion of the delivery fiber 115, lens processing is performed and the minute lens 130B is formed. Similarly, at the output end portion of the delivery fiber 125, lens processing is performed and the minute lens 140B is formed. That is, the delivery fibers 115 and 125 are so-called lensed fibers.

In the present embodiment, as an example, the lens 130B has a circular shape with a diameter $\varphi_3 = 0.25$ mm. Similarly, the lens 140B has a circular shape with a diameter $\varphi_4 = 0.25$ mm. By making the lenses 130B and 140B to be a circle with a diameter of 0.25 mm, it is possible to make the beam at the output end portion of the lenses 130B and 140B have a diameter of approximately 0.2 mm and a curvature radius of infinity.

In this case, for example, the point $P_1$, which is the light condensing position inside the terahertz wave generating element 160, is located at a position of $D_7 = 50$ mm from the output end portion (laser output end portion) of the lenses 130B and 140B. The oscillation wavelength of the terahertz wave $L_3$ to be generated is determined depending on the oscillation wavelength of the seed laser light source and the incident angle $\theta_1$ to the terahertz wave generating element 160. When the diameters $\varphi_3$ and $\varphi_4$ of the lenses 130B and 140B are 0.25 mm, an optical axis interval $D_8$ between the lenses cannot be brought to 0.25 mm or less, and therefore the incident angle $\theta_1$ is approximately 0.3° at minimum.

Similar to the first embodiment, it is possible to change the frequency of the terahertz wave $L_3$ to be generated, by changing the temperature of the seed laser light sources 111 and 121, and changing the incident angle $\theta_1$ so as to satisfy the phase matching condition. In the present embodiment, the changing of the incident angle $\theta_1$ is performed by rotating the delivery fiber 115 in which the lens 130B is formed, along a circular arc having a radius of 50 mm centering around the point $P_1$, which is the focal point of the laser beam $L_1$ and the laser beam $L_2$.

TABLE 2

| LASER BEAM $L_1$ WAVELENGTH (nm) | LASER BEAM $L_2$ WAVELENGTH (nm) | INCIDENT ANGLE $\theta_1$ (deg) | OPTICAL AXIS INTERVAL $D_8$ (mm) | TERAHERTZ WAVE $L_3$ FREQUENCY (THz) |
|---|---|---|---|---|
| 1063.42 | 1064.65 | 0.31 | 0.27 | 0.3 |
| 1060.00 | 1071.38 | 2.91 | 2.54 | 3.0 |

For example, as indicated in Table 2, when the frequency of the terahertz wave $L_3$ is 0.3 THz, the wavelength of the laser beam $L_1$ is to be set to 1063.42 nm, the wavelength of the laser beam $L_2$ is to be set to 1064.65 nm, and the incident angle $\theta_1$ is to be set to 0.31°. In this case, the optical axis interval $D_8 = 0.27$ mm. Furthermore, when the frequency of the terahertz wave $L_3$ is 3 THz, the wavelength of the laser beam $L_1$ is to be set to 1060.00 nm, the wavelength of the laser beam $L_2$ is to be set to 1071.38 nm, and the incident angle $\theta_1$ is to be set to 2.91°. In this case, the optical axis interval $D_8 = 2.54$ mm.

The incident angle changing means for adjusting the incident angle $\theta_1$ is not particularly limited as long as the incident angle changing means is a mechanical mechanism for circularly moving the delivery fiber 115 in which the lens 130B is formed. For example, a gonio stage or a rotating stage, etc., may be used. Furthermore, automatic position adjustment by a stepping motor, etc., may also be performed.

As described above, by forming the lenses 130B and 140B by performing lens processing at the output end portions of the delivery fibers 115 and 125, the laser light sources 110 and 120 can be disposed even more closer to each other than in the second embodiment. Thus, it is possible to simplify the optical system and further reduce the size of the terahertz wave generation apparatus 100B as compared with the terahertz wave generation apparatus 100A.

Fourth Embodiment

In a fourth embodiment, an example in which one of the laser light sources is a solid-state laser is indicated. Note that in the fourth embodiment, descriptions of the same elements as those in the embodiments described above, may be omitted.

Figure 11A:
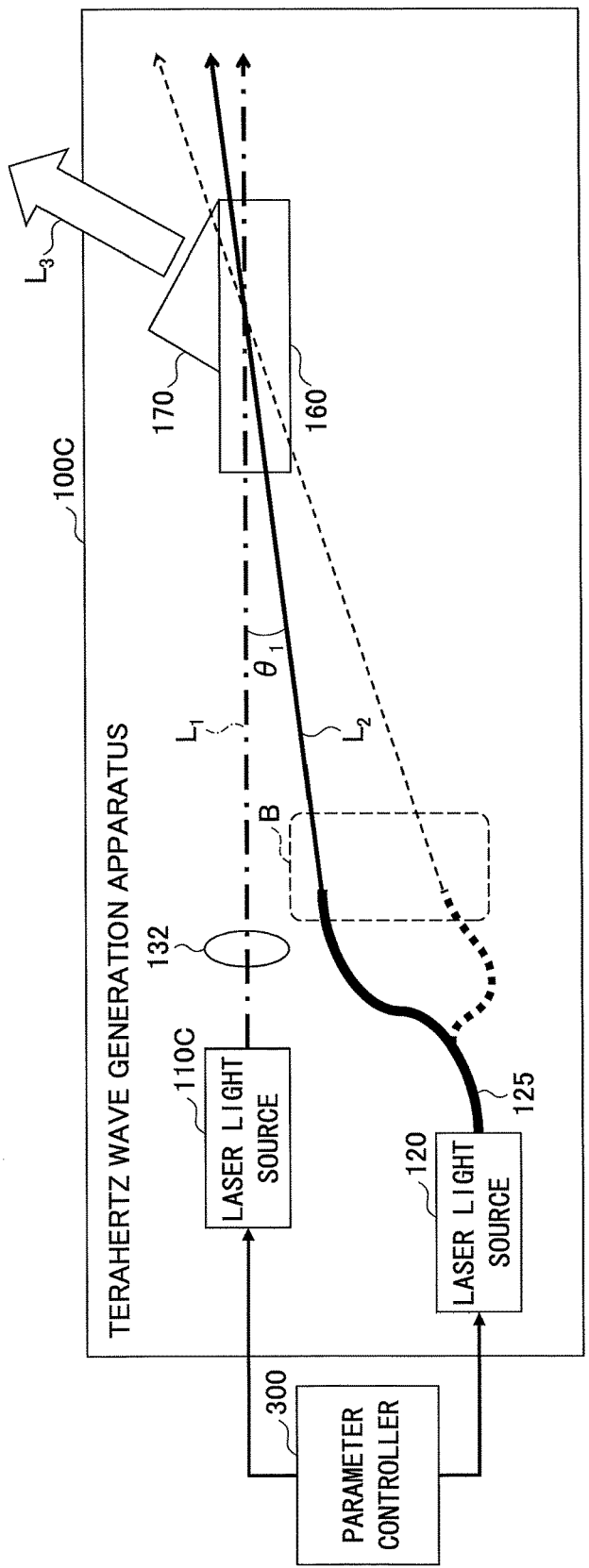
FIGS. 11A and 11B are diagrams illustrating an example of a configuration of a terahertz wave generation apparatus according to a fourth embodiment of the present invention.
Figure 11B:
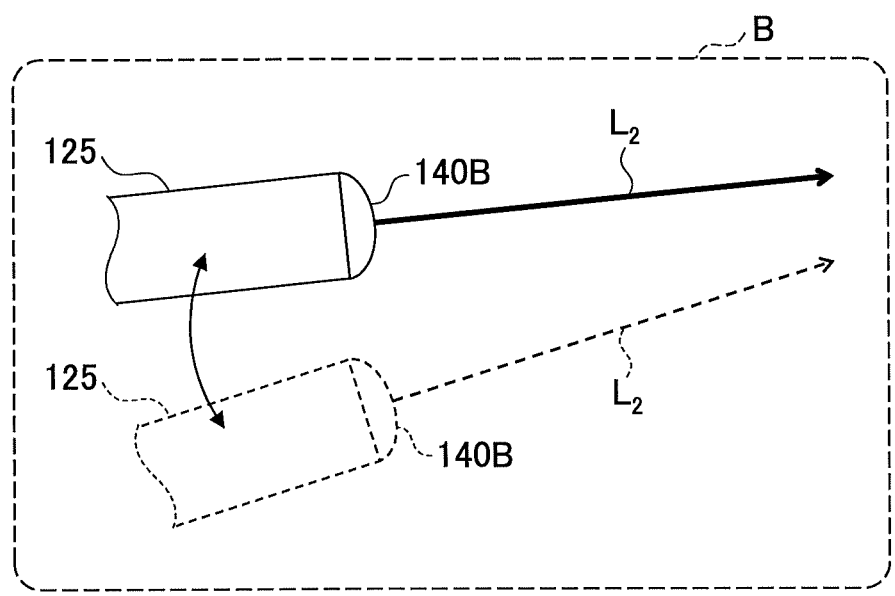

FIGS. 11A and 11B are diagrams illustrating an example of a configuration of a terahertz wave generation apparatus according to the fourth embodiment, wherein FIG. 11A is an overall view, FIG. 11B is an enlarged view of a portion B in FIG. 11A.

As illustrated in FIG. 11A, a terahertz wave generation apparatus 100C includes laser light sources 110C and 120, the lens 132, the lens 140B, the terahertz wave generating element 160, and the prism 170.

The laser light source 110C is, for example, a solid-state laser using Nd:YAG as a laser medium, and can have a wavelength of 1064 nm. However, this is merely an example, and the wavelength of the laser light source 110C may be 1030 nm or 1034 nm, etc. The optical axis of the laser light source 110C is fixed, and the laser beam $L_1$ emitted from the laser light source 110C is condensed by the lens 132 and enters the terahertz wave generating element 160 in parallel with the terahertz wave generating element 160. The laser light source 120, the delivery fiber 125, and the lens 140B are the same as those in the third embodiment. The delivery fiber 125 in which the lens 140B is formed is rotatable.

Note that as the laser light source 110C, instead of a solid laser using Nd:YAG as a laser medium, a solid laser using another laser medium may be used. Specifically, the laser light source 110C may be formed by using, for example, Nd:YLF, Yb:YAG, Yb:KGW, Nd:YVO$_4$, Er:YAG, and Tm:YAG.

The oscillation wavelength of the solid state laser is limited to be narrow by the medium, and therefore it is preferable to combine an optimum fiber laser light source according to the oscillation wavelength. For example, in Nd:YLF, Yb:YAG, Yb:KGW, Nd:YVO$_4$, the oscillation wavelength is in a limited range of 1000 nm to 1060 nm, and therefore it is preferable to use a fiber laser light source using an optical fiber in which Yb is doped in a fiber amplifier.

Furthermore, in the case of Er:YAG, it is preferable to use a fiber laser light source using an optical fiber in which Er is doped in a fiber amplifier. In the case of Tm:YAG, it is preferable to use a fiber laser light source using an optical fiber in which Tm is doped in a fiber amplifier.

In cases other than the above crystal, it is preferable to select an appropriate solid state laser and a fiber laser light source so that a combination of wavelengths satisfying the phase matching condition can be achieved.

Fifth Embodiment

In a fifth embodiment, an example is indicated in which the incident angle $\theta_1$ is adjusted by moving two delivery fibers in parallel. Note that in the fifth embodiment, descriptions of the same elements as those in the embodiments described above, may be omitted.

Figure 12B:
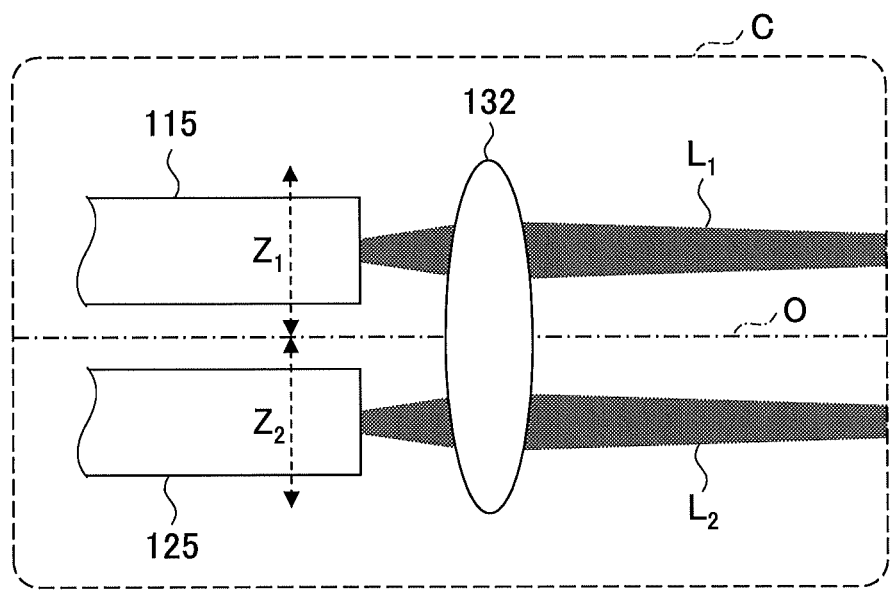

FIGS. 12A and 12B are diagrams illustrating an example of the configuration of a terahertz wave generation apparatus according to the fifth embodiment, wherein FIG. 12A is an overall view and FIG. 12B is an enlarged view of a portion C in FIG. 12A.

As illustrated in FIG. 12A, a terahertz wave generation apparatus 100D includes the laser light sources 110 and 120, the lens 132, the terahertz wave generating element 160, and the prism 170.

In the terahertz wave generation apparatus 100D, the delivery fibers 115 and 125 are disposed so that the optical axes of the delivery fibers 115 and 125 are parallel to each other. The laser beams $L_1$ and $L_2$ emitted from the delivery fibers 115 and 125 are condensed by a single lens 132 that is an optical member, and enter the terahertz wave generating element 160.

In this case, the elements are disposed such that the optical axis O of the lens 132 is the central axis, and the optical axes of the laser beams $L_1$ and $L_2$ are parallel to the optical axis O of the lens 132, and the optical axes of the laser beams $L_1$ and $L_2$ are equally spaced from the optical axis O of the lens 132. Accordingly, the laser beams $L_1$ and $L_2$ that have passed through the lens 132 intersect at one point at the position of the focal point of the lens 132.

The terahertz wave generating element 160 is set at the position of the focal point of the lens 132, and generates the terahertz wave $L_3$. When generating the terahertz wave $L_3$ having a different frequency, similar to the first embodiment, etc., the wavelengths of the laser beams $L_1$ and $L_2$ are to be changed so as to match the terahertz wave $L_3$ to be generated, and the incident angle $\theta_1$ is to be changed so as to satisfy the phase matching condition of the terahertz wave generating element 160.

In the present embodiment, at least one of the delivery fibers 115 and 125 is movable, such that the laser beams $L_1$ and $L_2$ are emitted in parallel with each other, and the space between the laser beams $L_1$ and $L_2$ can be changed. For example, in order to make the optical axes of the laser beams $L_1$ and $L_2$ constantly equally spaced from the optical axis O of the lens 132 while maintaining a parallel state of the optical axes of the laser beams $L_1$ and $L_2$ and the optical axis of the lens 132, the delivery fibers 115 and 125 are moved in the direction of arrows $Z_1$ and $Z_2$ (in opposite directions to each other with respect to the optical axis O), to adjust the incident angle $\theta_1$. The delivery fibers 115 and 125 may form a lensed fiber as illustrated in FIG. 10B.

Accordingly, when generating a different terahertz wave $L_3$, the optical axes of the laser beams $L_1$ and $L_2$ are to be linearly moved. Therefore, various elements for causing linear movement may be used as an incident angle changing means for adjusting the incident angle $\theta_1$. A linear motion stage is a typical element for causing linear movement, and it is easy to attach a motor to the linear motion stage for electrically motorizing the linear motion stage. Furthermore, it is also possible to use piezo or voice coil motor. A linear guide may also be used.

As described above, by moving the delivery fibers 115 and 125 in parallel by an incident angle changing means and condensing the laser beams emitted from the delivery fibers 115 and 125 by a single lens, the configuration is simplified and the terahertz wave generation apparatus can be further reduced in size. Furthermore, the delivery fibers 115 and 125 can be moved with high accuracy, and therefore it is possible to adjust the incident angle $\theta_1$ with high accuracy.

Sixth Embodiment

In a sixth embodiment, an example of a terahertz wave generation apparatus using difference frequency generation by collinear phase matching is indicated. Note that in the sixth embodiment, descriptions of the same elements as those in the embodiments described above, may be omitted.

Figure 13A:
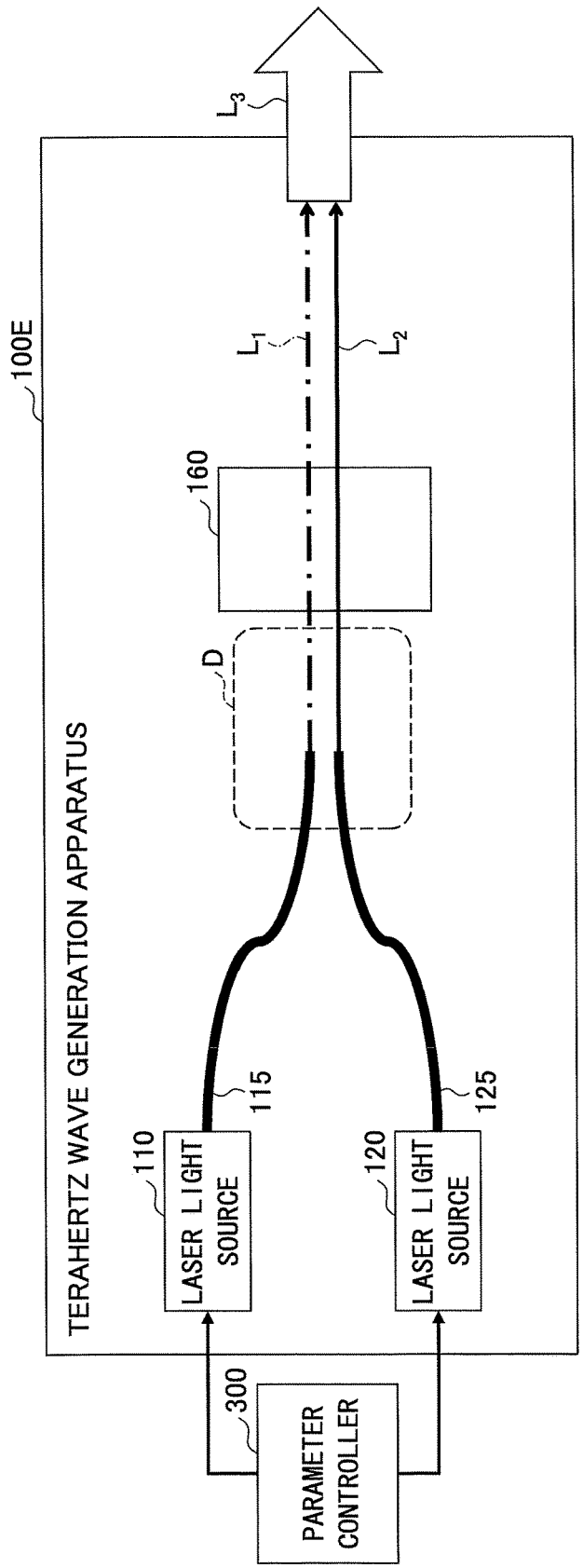
FIGS. 13A, 13B, and 13C are diagrams illustrating an example of a configuration of a terahertz wave generation apparatus according to a sixth embodiment of the present invention.
Figure 13B:
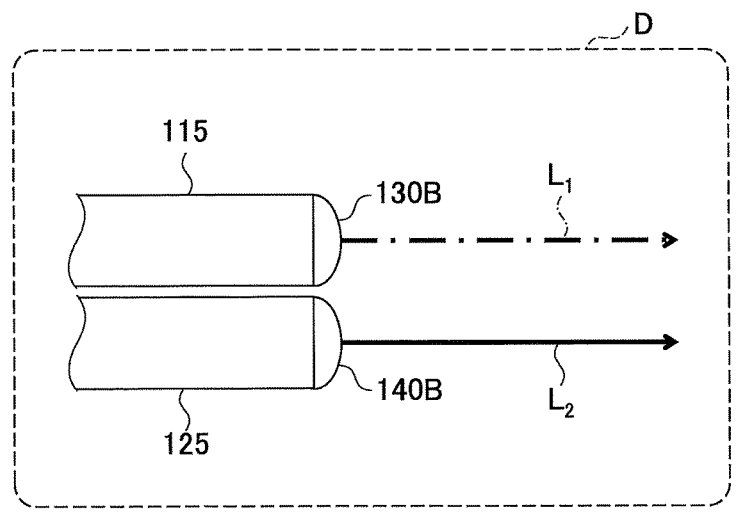
Figure 13C:
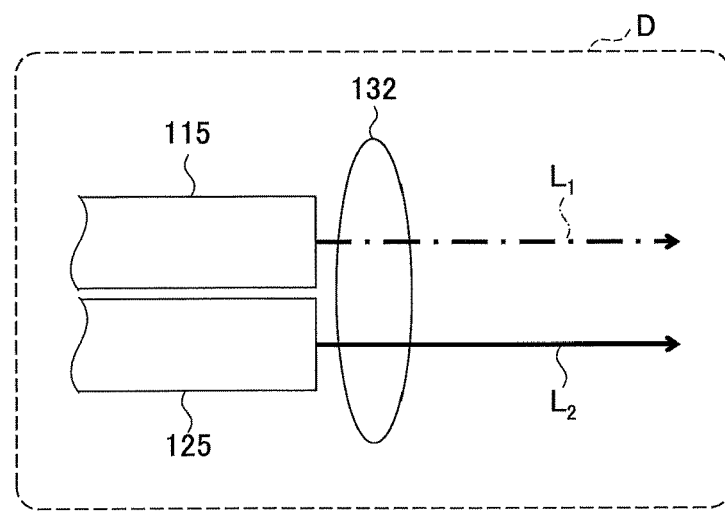

FIGS. 13A, 13B, and 13C are diagrams illustrating an example of a configuration of a terahertz wave generation apparatus according to the sixth embodiment, wherein FIG. 13A is an overall view, and FIGS. 13B and 13C are enlarged views of a portion D in FIG. 13A.

As illustrated in FIG. 13A, a terahertz wave generation apparatus 100E includes the laser light sources 110 and 120 and the terahertz wave generating element 160.

In the terahertz wave generation apparatus 100E, the delivery fibers 115 and 125 are disposed so that the optical axes of the delivery fibers 115 and 125 are parallel to each other. As illustrated in FIG. 13B, lens processing may be performed on the output end portions of the delivery fibers 115 and 125 to form the lenses 130B and 140B. In an another example as illustrated in FIG. 13C, the laser beams $L_1$ and $L_2$ emitted from the delivery fibers 115 and 125 may be condensed by a single lens 132.

In both cases of FIG. 13B and FIG. 13C, the laser beams $L_1$ and $L_2$ that are parallel to each other enter the terahertz wave generating element 160 to generate the terahertz wave $L_3$.

In the terahertz wave generation apparatus 100E, a DAST crystal (4-N, N-dimethylamino-4'-N'-methylstilbazolium tosylate) is used as the terahertz wave generating element 160. A DAST crystal that is an organic nonlinear crystal has a large nonlinearity that is not found in conventional inorganic nonlinear crystals, and is thus effective for generating terahertz waves.

The DAST crystal performs differential frequency generation (DFG) satisfying the collinear phase matching condition for generation of the terahertz wave. In this case, the terahertz wave $L_3$ is generated in substantially the same direction as the optical axes of the laser beams $L_1$ and $L_2$, and therefore it is possible to achieve a light source that is compact and easy to handle.

Note that as the terahertz wave generating element 160, a BNA crystal (N-benzyl-2-methyl-4-nitroaniline) may be used instead of the DAST crystal. By using a DAST crystal or a BNA crystal as the terahertz wave generating element 160, it is possible to generate a terahertz wave having high efficiency and a broad band.

Seventh Embodiment

In a seventh embodiment, another example of a terahertz wave generation apparatus using difference frequency generation by collinear phase matching is indicated. Note that in the seventh embodiment, descriptions of the same elements as those in the embodiments described above, may be omitted.

Figure 14:
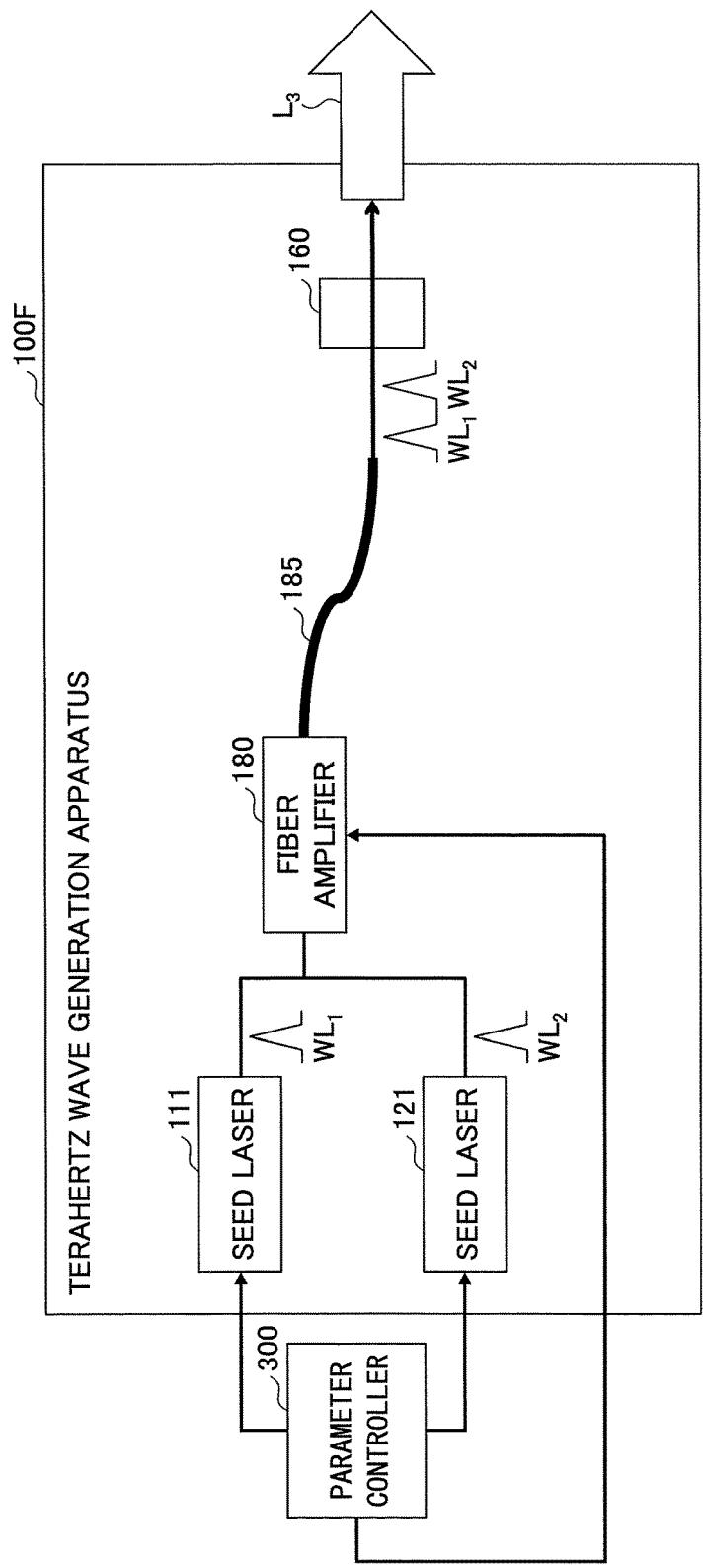
FIG. 14 is a diagram illustrating an example of a configuration of a terahertz wave generation apparatus according to a seventh embodiment of the present invention.

FIG. 14 is a diagram illustrating an example of a configuration of a terahertz wave generation apparatus according to the seventh embodiment.

As illustrated in FIG. 14, a terahertz wave generation apparatus 100F includes the seed laser light sources 111 and 121, a fiber amplifier 180, and the terahertz wave generating element 160.

Similar to the case of FIG. 3, for example, the fiber amplifier 180 may include the preamplifiers $112_1$, $112_2$, and $112_3$ connected in series, and the main amplifier 113. Similar to the sixth embodiment, a DAST crystal or a BNA crystal may be used as the terahertz wave generating element 160.

In the terahertz wave generation apparatus 100F, a laser beam $WL_1$ from the seed laser light source 111 and a laser beam $WL_2$ from the seed laser light source 121 have different wavelengths, and are combined before entering the fiber amplifier 180. The laser beam including the two wavelengths after the combination, is amplified to a high output by the fiber amplifier 180, and then the laser beam enters the terahertz wave generating element 160 via a delivery fiber 185, and the terahertz wave $L_3$ is generated by the terahertz wave generating element 160.

As described above, in the terahertz wave generation apparatus 100F, a laser beam, which includes two wavelengths for generating a desired terahertz wave $L_3$ from the fiber amplifier 180, is to be input to the DAST crystal or the BNA crystal, and the terahertz wave $L_3$ can be easily obtained without involving complex optical adjustment.

Furthermore, the number of seed laser light sources may be further increased. In this case, high-speed switching of the terahertz wave $L_3$ in a stepwise manner becomes possible by switching a plurality of seed laser light sources at high speed.

Note that in the terahertz wave generation apparatus 100F, the seed laser light source 111 and the fiber amplifier 180 function in the same manner as the laser light source 110, and the seed laser light source 121 and the fiber amplifier 180 function in the same manner as the laser light source 120. That is, the seed laser light sources 111 and 121 and the fiber amplifier 180 are fiber laser light sources capable of independently controlling the parameters of the seed laser light sources 111 and 121.

Eighth Embodiment

In an eighth embodiment, an example of an inspection apparatus provided with a terahertz wave generation apparatus is indicated. Note that in the eighth embodiment, descriptions of the same elements as those in the embodiments described above, may be omitted.

Figure 15:
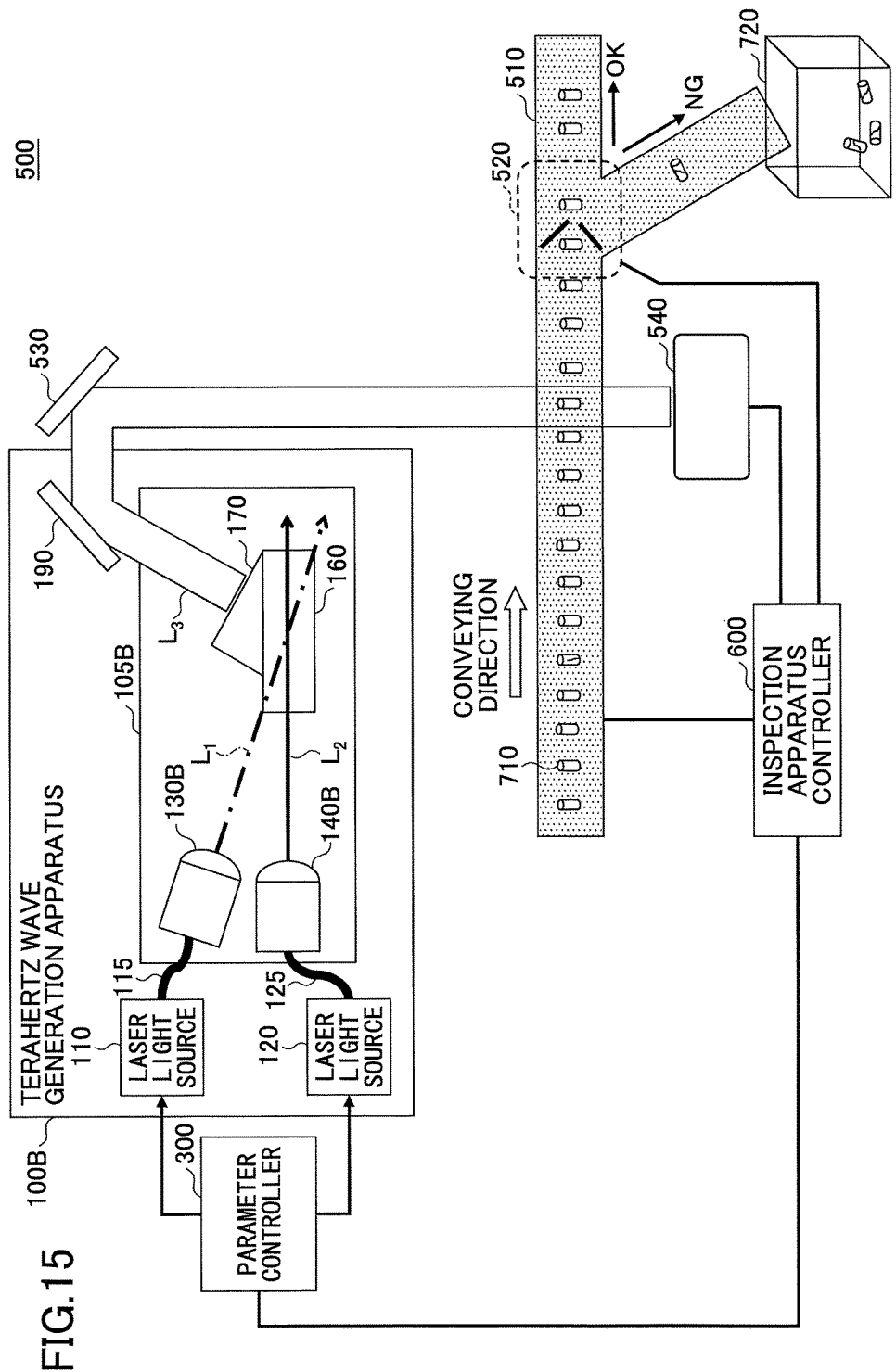
FIG. 15 is a diagram illustrating an example of a configuration of an inspection apparatus according to an eighth embodiment of the present invention.

FIG. 15 is a diagram illustrating an example of a configuration of an inspection apparatus according to the eighth embodiment. As illustrated in FIG. 15, an inspection apparatus 500 includes the terahertz wave generation apparatus 100B, the parameter controller 300, a belt conveyer 510, a determining unit 520, a mirror 530, a light receiving element 540, and an inspection apparatus controller 600. A reference numeral 710 denotes an object to be inspected (inspection target object), and a reference numeral 720 denotes an NG (defective) item recovery box. The NG item recovery box 720 may be provided according to need.

Figure 16:
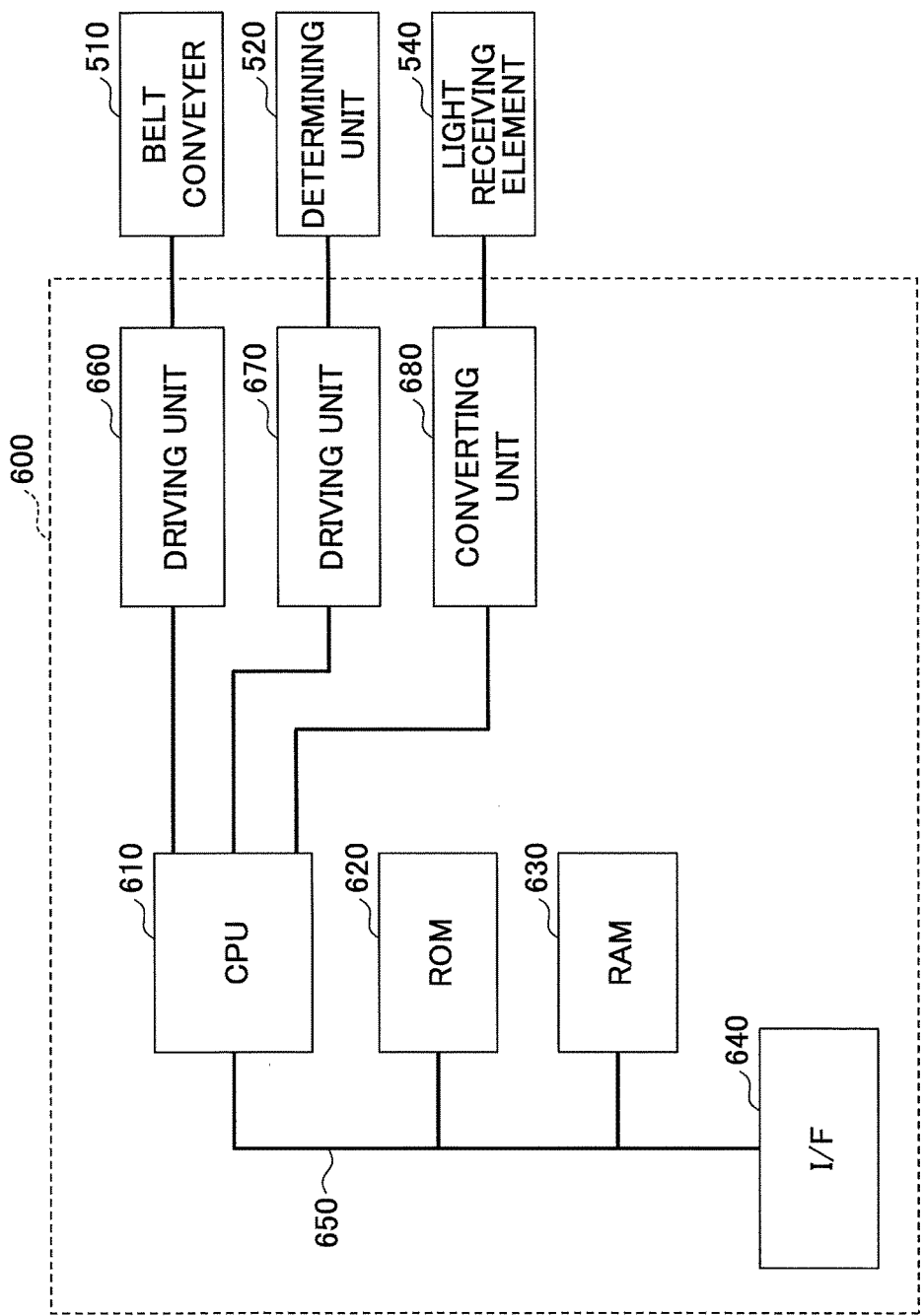
FIG. 16 is an example of a hardware block diagram of the inspection apparatus controller according to the eighth embodiment of the present invention.

FIG. 16 is an example of a hardware block diagram of the inspection apparatus controller. As illustrated in FIG. 16, the inspection apparatus controller 600 includes, for example, a central processing unit (CPU) 610, a read-only memory (ROM) 620, a random access memory (RAM) 630, an interface (I/F) 640, a bus line 650, driving units 660 and 670, and a converting unit 680. The CPU 610, the ROM 620, the RAM 630, and the I/F 640 are mutually connected via a bus line 650.

The CPU 610 controls the respective functions of the inspection apparatus controller 600. The ROM 620 that is a storage means stores programs executed by the CPU 610 to control the respective functions of the inspection apparatus controller 600 and various kinds of information. The RAM 630 that is a storage means is used as a work area, etc., of the CPU 610.

Furthermore, the RAM 630 can temporarily store predetermined information. The I/F 640 is an interface for connecting the inspection apparatus controller 600 to another apparatus, etc. The inspection apparatus controller 600 may be connected to an external network, etc., via the I/F 640.

The CPU 610 of the inspection apparatus controller 600 is configured to be able to transmit and receive signals to and from the CPU 310 of the parameter controller 300. Part or all of the inspection apparatus controller 600 and the parameter controller 300 may be implemented as one controller.

Figure 17:
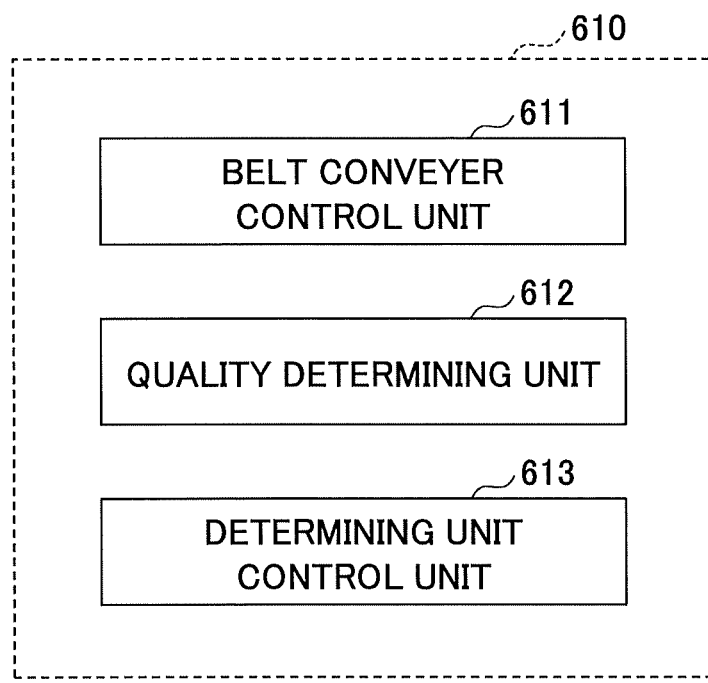
FIG. 17 is an example of a functional block diagram of a CPU of an inspection apparatus controller according to the eighth embodiment of the present invention.

FIG. 17 is an example of a functional block diagram of the CPU of the inspection apparatus controller. As illustrated in FIG. 17, the CPU 610 includes, as functional blocks, a belt conveyer control unit 611, a quality determining unit 612, and a determining unit control unit 613. The CPU 610 may include other appropriate functional blocks.

The belt conveyer control unit 611 sends a driving signal to the driving unit 660 so as to control or stop the conveyance speed of the belt conveyer 510. A sensor for detecting the conveying speed of the belt conveyer 510 may be provided.

The quality determining unit 612 can determine the quality of the inspection target objects 710 disposed at predetermined intervals on the belt conveyor 510 and conveyed at a high speed. Specifically, in the converting unit 680, a terahertz wave, which is detected by the light receiving element 540, is converted into a signal type and a signal level that can be handled by the CPU 610, and the terahertz wave is input to the CPU 610 as a quality determining signal. The quality determining unit 612 determines the quality of the inspection target object 710 on the basis of the quality determining signal.

The determining unit control unit 613 can send a driving signal to the driving unit 670 based on the quality determination result of the quality determining unit 612, to rotate the determining unit 520 by a motor, etc., so as to switch the conveyance destination of the inspection target object 710 on the belt conveyor 510.

Figure 18:
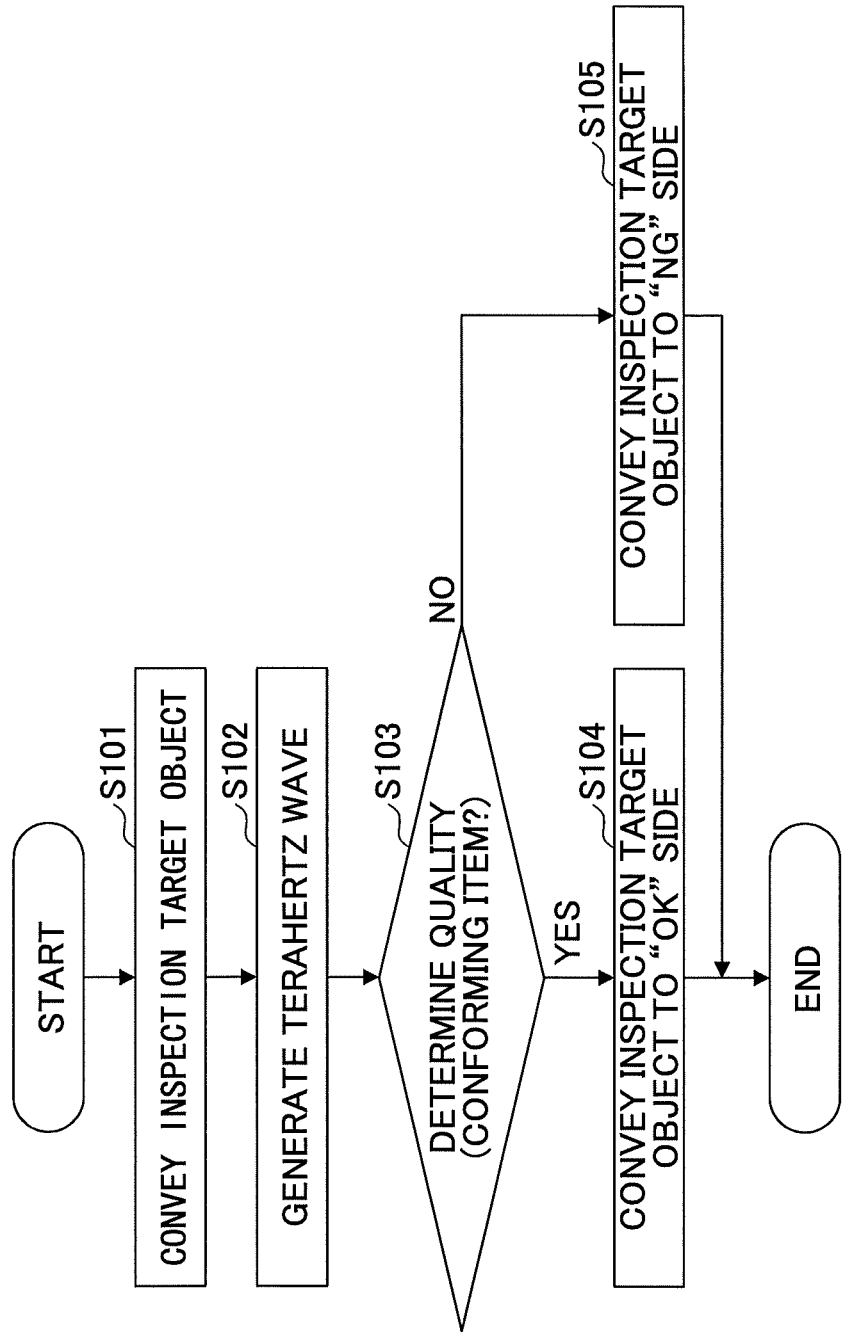
FIG. 18 is an example of a flowchart for describing the operation of the inspection apparatus according to the eighth embodiment of the present invention.

FIG. 18 is an example of a flowchart for describing the operation of the inspection apparatus according to the eighth embodiment.

As illustrated in FIG. 18, first, in step S101, the belt conveyer control unit 611 of the inspection apparatus controller 600 sends a driving signal to the driving unit 660, and starts conveying the inspection target objects 710 disposed at predetermined intervals on the belt conveyer 510.

Next, in step S102, the timing control unit 311 of the parameter controller 300 causes the laser light sources 110 and 120 to emit the laser beams $L_1$ and $L_2$ at a predetermined timing to generate the terahertz wave $L_3$. The terahertz wave $L_3$ is reflected by a mirror 190 provided in the terahertz wave generation apparatus 100B, and is further reflected by the mirror 530, and sequentially irradiates the inspection target objects 710 that are conveyed at high speed on the belt conveyor 510. The terahertz wave $L_3$ that has passed through the inspection target object 710 is received by the light receiving element 540.

Next, in step S103, the quality determining unit 612 of the inspection apparatus controller 600 determines the quality of the inspection target object 710 based on the quality determining signal received by the light receiving element 540 and converted by the converting unit 680. For example, in the case where the inspection target object 710 is an organic substance, it is possible to detect the inclusion of a foreign substance such as metal in the inspection target object 710. That is, although the terahertz wave $L_3$ is permeable to many organic substances, the permeability of the terahertz wave $L_3$ is low with respect to specific substances such as a metal. Therefore, the quality determining unit 612 determines the inspection target object 710 to be a conforming item when the quality determining signal is greater than or equal to a threshold set in advance, and determines the inspection target object 710 to be a defective item when the quality determining signal is less than the threshold.

An example of the inspection target object 710 is food; however, the inspection target object 710 may be a tablet, etc. That is, as long as there is a significant difference in the permeability of the terahertz wave $L_3$ between the inspection target object and a specific substance, it is possible to inspect the inclusion of the specific substance in the inspection target object.

In step S103, when the quality determination result of the quality determining unit 612 is "conforming item", the process proceeds to step S104. In step S104, the determining unit control unit 613 of the inspection apparatus controller 600 rotates the determining unit 520 based on the quality determination result of the quality determining unit 612, and switches the conveyance destination of the inspection target object 710 on the belt conveyor 510 to an "OK" arrow direction.

In step S103, when the quality determination result of the quality determining unit 612 is "defective item", the process proceeds to step S105. In step S105, the determining unit control unit 613 of the inspection apparatus controller 600 rotates the determining unit 520 based on the quality determination result of the quality determining unit 612, and switches the conveyance destination of the inspection target object 710 on the belt conveyor 510 to an "NG" arrow direction. The inspection target objects 710 conveyed in the "NG" arrow direction are sequentially stored in the NG item recovery box 720.

Note that although FIG. 18 illustrates the flow of a single quality determining operation, in reality, the quality determination is repeatedly executed as many times as required.

As described above, the terahertz wave generation apparatus 100B can be used for the inspection apparatus 500 that inspects the inclusion of a specific substance in an inspection target object. Instead of the terahertz wave generation apparatus 100B, the terahertz wave generation apparatuses 100A and 100C to 100F may be used.

Although the preferred embodiments have been described in detail above, the present invention is not limited to the above-described embodiments, and various modifications and substitutions may be made to the above-described embodiments without departing from the scope of the claims.

For example, the embodiments may be appropriately implemented in combination.

Furthermore, in each embodiment, a fiber laser other than the MOPA method may be used. An example of a fiber laser other than the MOPA method, is a pulsed fiber laser using a Q switch. However, some fiber lasers other than the MOPA method cannot control some parameters such as the pulse width, and therefore the MOPA type fiber laser is most superior in parameter controllability Furthermore, the parameter controller 300 may be incorporated in the terahertz wave generation apparatus.

According to one embodiment of the present invention, a terahertz wave generation apparatus having excellent parameter controllability, is provided.

The terahertz wave generation apparatus and the inspection apparatus are not limited to the specific embodiments described in the detailed description, and variations and modifications may be made without departing from the spirit and scope of the present invention.

What is claimed is:

1. A terahertz wave generation apparatus comprising:
a plurality of fiber laser light sources configured to generate laser beams respectively having different wavelengths; and
a terahertz wave generating element configured to receive the laser beams having different wavelengths and generate a terahertz wave from the laser beams,
wherein the plurality of fiber laser light sources include fiber laser light sources respectively including parameters that can be controlled independently, and the terahertz wave generating element includes a nonlinear optical crystal, said parameters being at least one of a pulse width, a repetition frequency and movements of the fiber laser light sources that emit the laser beams, and
wherein the terahertz wave generation apparatus is configured to change an incident angle at which the laser beams enter the terahertz wave generating element by controlling the movements of the fiber laser light sources that emit the laser beams.

2. The terahertz wave generation apparatus according to claim 1, wherein the nonlinear optical crystal includes lithium niobate.

3. The terahertz wave generation apparatus according to claim 1, wherein the nonlinear optical crystal includes MgO-doped lithium niobate.

4. The terahertz wave generation apparatus according to claim 1, wherein the nonlinear optical crystal includes gallium phosphide.

5. The terahertz wave generation apparatus according to claim 1, wherein the laser beams having different wavelengths are emitted in parallel to each other, and distances between the laser beams can be changed.

6. The terahertz wave generation apparatus according to claim 5, wherein the laser beams respectively emitted from the fiber laser light sources are condensed by a single optical member.

7. The terahertz wave generation apparatus according to claim 1, wherein the nonlinear optical crystal includes a 4-N,N-dimethylamino-4'-N'-methylstilbazolium tosylate or a N-benzyl-2-methyl-4-nitroaniline.

8. An inspection apparatus comprising:
   the terahertz wave generation apparatus according to claim 1, wherein
   the inspection apparatus is configured to irradiate an inspection target object with the terahertz wave generated by the terahertz wave generating element, and inspect the inspection target object.

9. The terahertz wave generation apparatus according to claim 1, wherein said at least one of the plurality of fiber laser light sources include the fiber laser light sources configured to control the pulse width.

10. The terahertz wave generation apparatus according to claim 1, wherein said at least one of the plurality of fiber laser light sources include the fiber laser light sources configured to control the repetition frequency.

\* \* \* \* \*